US008262715B2

(12) United States Patent
Wong, Jr. et al.

(10) Patent No.: US 8,262,715 B2
(45) Date of Patent: Sep. 11, 2012

(54) MEDICAL DEVICE AND METHOD FOR TEMPERATURE CONTROL AND TREATMENT OF THE EYE AND SURROUNDING TISSUES VIA MAGNETIC DRUG THERAPY

(75) Inventors: Edward K. Wong, Jr., Newport Beach, CA (US); Timothy L. Lee, Koloa, HI (US); Markus D. Wong, Newport Beach, CA (US); Michael T. Vu, Newport Coast, CA (US)

(73) Assignee: Eye Delivery System, LLC, Newport Beach, CA (US)

( * ) Notice: Subject to any disclaimer, the term of this patent is extended or adjusted under 35 U.S.C. 154(b) by 1480 days.

(21) Appl. No.: 11/746,621

(22) Filed: May 9, 2007

(65) Prior Publication Data
US 2007/0282405 A1  Dec. 6, 2007

Related U.S. Application Data

(63) Continuation-in-part of application No. 11/285,690, filed on Nov. 22, 2005, now Pat. No. 7,229,468.

(60) Provisional application No. 60/630,806, filed on Nov. 23, 2004.

(51) Int. Cl.
*A61F 7/00* (2006.01)
(52) U.S. Cl. ........................................... 607/104
(58) Field of Classification Search ............ 604/20, 604/104, 108, 294; 607/104, 108; 606/20
See application file for complete search history.

(56) References Cited

U.S. PATENT DOCUMENTS

| | | | |
|---|---|---|---|
| 4,387,707 A * | 6/1983 | Polikoff | 601/37 |
| 4,564,016 A * | 1/1986 | Maurice et al. | 604/20 |
| 6,024,095 A * | 2/2000 | Stanley, III | 128/898 |
| 6,154,671 A * | 11/2000 | Parel et al. | 604/20 |
| 6,319,240 B1 | 11/2001 | Beck | |
| 6,918,904 B1 * | 7/2005 | Peyman | 606/5 |
| 2002/0147424 A1 * | 10/2002 | Ostrow et al. | 604/20 |
| 2005/0260153 A1 | 11/2005 | Calias et al. | |
| 2006/0136022 A1 | 6/2006 | Wong, Jr. et al. | |
| 2006/0142706 A1 | 6/2006 | Roy et al. | |
| 2007/0093742 A1 | 4/2007 | Higuchi et al. | |

* cited by examiner

*Primary Examiner* — Kevin C Sirmons
*Assistant Examiner* — Michael J Anderson
(74) *Attorney, Agent, or Firm* — Walter A. Hackler

(57) ABSTRACT

The invention provides a medical device having a thermostat for temperature measurement, irrigation/aspiration ports for fluid exchange and application of therapeutic modalities, a pressure manometer for pressure measurement, and an external system for control of temperature, pressure, and flow rate. When applied to the eye, eyelid and orbit, this device can be used in hypothermia or hyperthermia applications, the control of intraocular pressure (IOP), and the application of treatment modalities. Methods of using the device in treating patients suffering from central retinal artery occlusion, anterior optic nerve disease, pathology of the choroid and retina including the macula, inflammation of the eye including the vitreous and anterior segment, glaucoma, inflammation and/or infections of the anterior and/or posterior segment of the eye, treatment before/during/after surgery of the eye, and the application of treatment modalities including iontophoresis through a semi-permeable membrane are described.

15 Claims, 20 Drawing Sheets

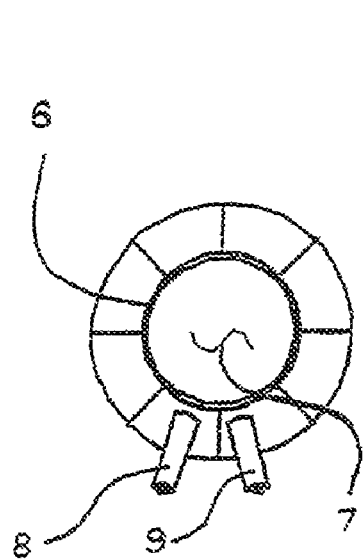
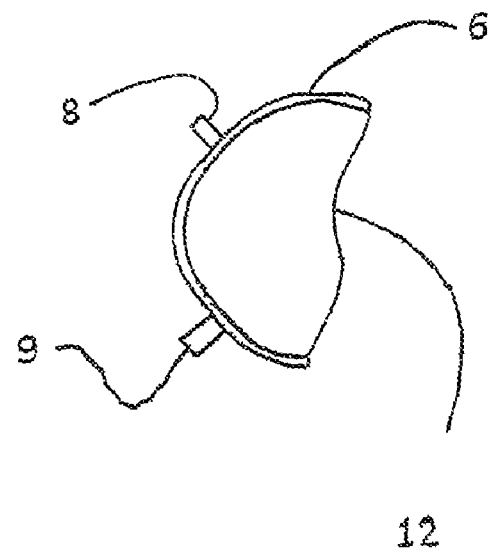
Fig 2   Fig 3
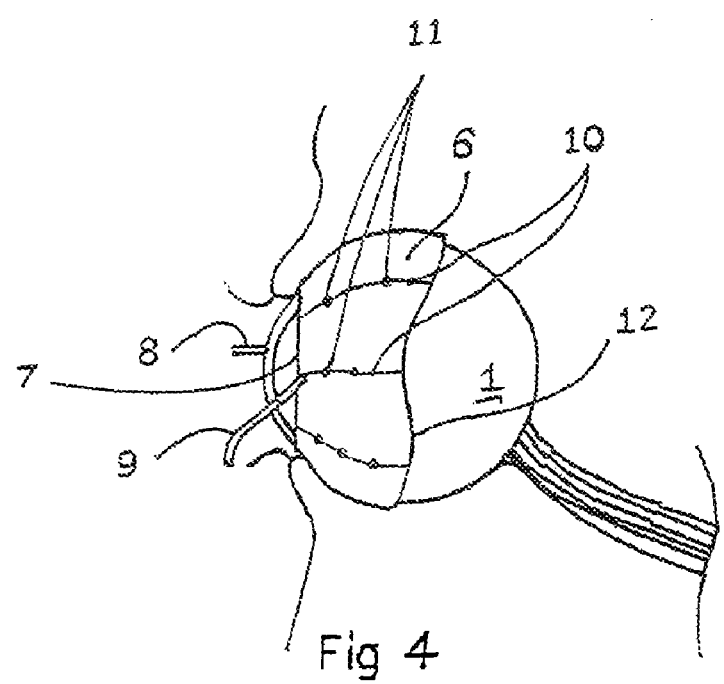
Fig 4

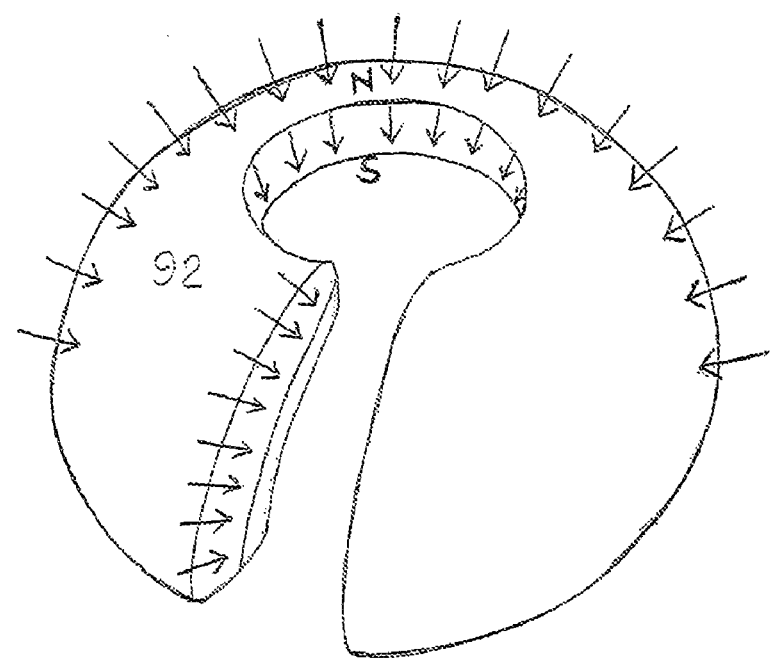
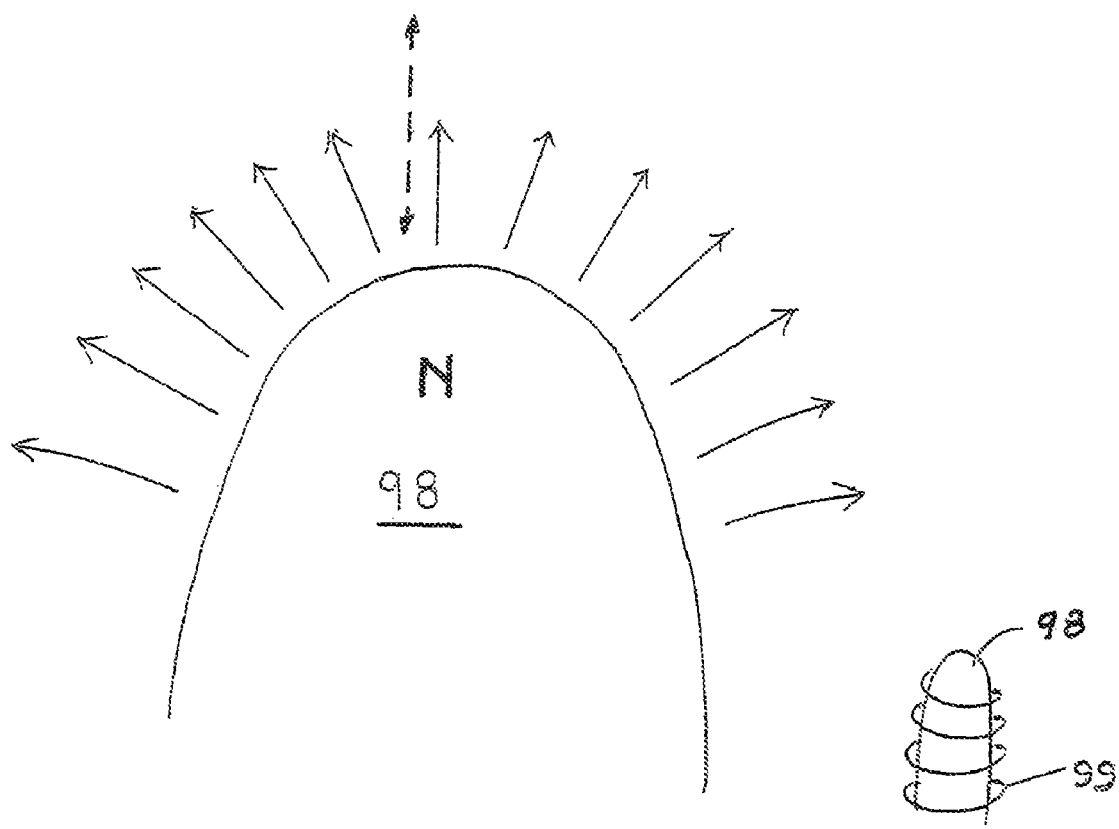
Fig 34
Fig 34a

MEDICAL DEVICE AND METHOD FOR TEMPERATURE CONTROL AND TREATMENT OF THE EYE AND SURROUNDING TISSUES VIA MAGNETIC DRUG THERAPY

The present application is a continuation-in-part of U.S. Ser. No. 11/285,690 filed Nov. 22, 2005 now U.S. Pat. No. 7,229,468 which claims priority of U.S. Ser. No. 60/630,806 filed Nov. 23, 2004 all incorporated herewith in their entirety.

FIELD OF THE INVENTION

The present invention generally relates to medical devices useful in reducing and preventing injury to the eye, the eyelids, the optic nerve and orbit by inducing local temperature control of the tissue and by administering a constant source of medication(s). More specifically, the invention provides devices for surrounding the exterior surface of the eye for use in hypothermia or hyperthermia applications, the rapid flow of fluid using conduction and convection principles, the application of treatment modalities and delivery of medications, the facilitated administration of medicaments via iontophoresis or other means, and the transmission of temperature control to other tissues of the orbit including the adnexae, the optic nerve, and extra-ocular muscles. The medical device has a thermister for temperature measurement, irrigation/aspiration ports for fluid exchange and application of therapeutic modalities, and a flexible inflatable unit that surrounds the external surface of the eye. An external system for control of temperature, pressure and flow rate is described. A method and a device capable of concurrent thermal regulation and iontophoresis by mild electric forces through the sclera where ionic permeability is facilitated by thinner equatorial sclera are also described. A method and a device capable of concurrent thermal regulation and delivery of charged medicaments facilitated by magnets or magnetic fields are also described. A method and device for thermal regulation by thermoelectrocoupling is described. A thermal regulating device that can also effectively deliver anesthetics non-invasively to the eyeball, eyelids and periorbita is also described.

BACKGROUND OF THE INVENTION

Lack of blood flow (ischemia) to the eye may result in death of the tissues in the optic nerve and retina/choroid. In the case of central retinal artery occlusion (CRAO), there is a particle (embolus) in the major blood vessel giving oxygen and nutrients to the retina. In the case of anterior ischemic optic neuropathy (AION), there may be an occlusion of the blood vessel(s) entering the eye in the anterior optic nerve. With optic neuritis (ON) involving the anterior optic nerve, there is an inflammation of the optic nerve due to disease in the myelin sheath, the covering of the nerve fibers that exit the eye. After a period of time (minutes to hours to days), death of the tissue may occur causing irreversible damage.

Pathology to tissues of the eye may occur due to blunt injuries, such as a blow to the eye/orbit, resulting in hemorrhage within or around the eye and associated swelling of eye tissue. Unfortunately, it is often difficult to control injury to the eye using conventional opthalmological means including medical and surgical intervention.

Various other diseases of the eye and the orbit may result in swelling of tissue with consequent loss of function. Inflammation of orbital tissue is usually managed with systemic medical therapy or even surgical decompression. Other types of inflammation of the tissues within the eye include posterior uveitis, choroiditis, retinitis, vitritis, scleritis, thyroid-related eye disease, phacoanaphylaxis, anterior uveitis, and sympathetic ophthalmia. Secondary glaucoma may result from inflammation involving the anterior segment of the eye.

Infections of the eye may involve the cornea, the sclera, the vitreous, the retina/choroid, the ciliary body, the lens, and the anterior chamber. They are usually treated with systemic antibiotics, occasionally systemic steroids, and topical drops of antibiotics, and intraocular antibiotic injections.

Current treatment for swelling or inflammation of the eye and orbit is not always satisfactory. In the severely injured eye or orbit, medical therapy to control swelling is usually applied systemically resulting in high levels of medication in the rest of the body with very low concentrations reaching the eye or orbit. Surgical intervention to decompress the eye and/or orbit requires major intervention through opening the bony walls of the orbit or skull to expose the area and prevent compression against the fixed volume of the bony walls. In the case of severe swelling of the sheath around the optic nerve, surgical decompression of the sheath has been attempted in severe cases of papilledema, anterior ischemic optic neuropathy, and severe trauma. The results have variable reports of success and failure of the procedures.

Age-related macular degeneration (AMD) is by far the most common cause of severe central vision loss in the Western World and has a profound effect on older adult daily activities. Age-related macular degeneration is an age and light related stress to macular cells, which break down and scar down. The dry form accounts for roughly eighty to ninety percent of all cases of AMD. The wet form of AMD or neovascular AMD, the other ten to twenty percent of all cases of AMD, involves abnormal blood vessel formation under the macula leading to subretinal fluid, subretinal hemorrhage and severe macular scarring. Wet age-related macular degeneration affects roughly 1.2 to 2 million people in the United States alone. Currently, around 8.2% of Americans over eighty years in age have wet AMD. Macular degeneration is more prevalent among white women, with more than 15% older than 80 years having wet AMD and/or geographic atrophy. Aging baby boomers will lead to higher prevalence of wet AMD in the next decades.

Most untreated eyes quickly deteriorate to less than 20/200 vision and eventually only counting-finger vision. Steroids and anti-angiogenic factors such as anti-VEGF (anti-vascular endothelial growth factor) have been used to suppress neovascularization. Anti-VEGF treatments currently available include ranibizumab (Lucentis) and pegaptanib sodium (Macugen). Lucentis is an antibody fragment that binds to VEGF and inhibits its activity. Macugen, an anti-VEGF aptamer that binds to one particular form of VEGF in the eye, neutralizes its activity. Lucentis has been especially promising. For example, Lucentis improves vision in 33% of patients with minimally classic or occult neovascularization at two years into treatment. Other monoclonal antibodies, anti-vectus techniques and other biologic factors will be available in the near future. The current method of anti-angiogenic administration is intra-vitreal injection, which is invasive and puts the eye at risk for endophthalmitis, detached retina, and scarring. A better delivery technique is needed.

Hypothermia has proved encouraging in the recent literature for the purpose of decreasing oxygen consumption and for decreasing swelling of the brain and other central nervous system (CNS) tissue. Since the eye is part of the CNS, it seems logical that hypothermia of the eye may decrease swelling of the eye and optic nerve in the same way as hypothermia of the brain prevents brain swelling. Unfortunately, cooling of the entire body to cool the brain does have inherent dangers, and similarly cooling of the eye by cooling the body may also have deleterious effects. The heart responds to hypothermia with arrhythmias, and the blood clotting mechanisms may be severely impaired resulting in hemorrhage. Moreover, cooling the body only results in a few degrees of cooling of the CNS. In the case of the eye, attempts have been made to cool the vitreous of the eye during retinal and vitreous surgery by surgically entering the eye and cooling it from within. A recent animal study on viability of CNS tissue of the eye after hypothermia demonstrated similar preservation of function.

Cooling the eye, eyelids, periorbita and orbits from the outside surface without surgery can decrease inflammation, minimize apoptosis and ischemic injury without the usual complications of invasive modalities. Thermal regulation of the eye when combined with other treatment modalities may further improve treatment outcome. For example, hypothermia in combination with ionotophoresis, can offer unique treatment results not previously attainable. Iontophoresis through the thin equatorial sclera of the eye can potentially improve intraocular delivery of medications.

Iontophoresis is a non-invasive technique for infusing charged molecules, medications, and other biochemicals into biological tissues via a weak electric current. A weak electrical charge, when applied to a permeable iontophoretic medicament chamber containing similarly charged molecules in solvent, gel vehicle, gel sponges, cross-linked hydrogels or other matrixes, will repel these charged particles into the neighboring tissue. This movement is controlled by the Lorentz force within this weak electric field created around this weak electric current.

Iontophoresis is currently not a commercially available therapeutic modality for the eye. There are now many drugs available to the eye physician who would prefer to deliver them safely to the entire eye, the posterior segment of the eye, the posterior orbit and optic nerve. Topical eye drops deliver medications to the ocular surface including the cornea and conjunctiva; corneal absorption is very poor for some medications due to the lipophilic corneal barrier. Systemic injection and oral administration of medications, which can be associated with many potential systemic side effects and adverse reactions, may yield very low drug concentration to the back of the eye, the vitreous cavity, the posterior orbit and the optic nerve. Subconjunctival and subtenon's injections are usually associated with a significant amount of medicament carried away by the rich conjunctival and Tenon's vasculature. Intraocular injections, such as vitreous injections and intra-cameral injections, carry risks of intraocular infection, bleeding, retinal complications and other iatrogenic adverse effects. Orbital injections, including peri-bulbar and retro-bulbar injections, are still invasive and associated with potential complications including retro-bulbar or peri-bulbar hemorrhage and infection. It may be difficult to control a constant administration of the medication over a predictable desired duration. An example is the long term elevation of intraocular pressure following a subconjunctival or intra-vitreal injection of depo-steroid.

Prior attempts to deliver medications via transcorneal iontophoresis were associated with very low vitreous drug concentrations and considerable systemic drug concentrations. The pitfalls were partially due to the failure to recognize that it would be best to avoid the lipophyllic cornea which is poorly peameable to some medications. U.S. Pat. No. 6,319,240 by Beck continued to teach the placement of the medicament chamber of the ocular iontophoresis device on the cornea. This patent recognized the permeability of the sclera but, rather than suggesting that the permeable sclerae be used for entry and delivery of medications, the embodiments described in this patent primarily involved corneal delivery techniques. They observed that medicaments and electric currents were diverted along the paths of least resistance on the ocular surface and away from the eye to other more vascularized peri-orbital soft tissues. Scleral barriers are described in the patent to keep the medications from escaping to the surrounding eyelids and peri-orbital tissues. This same patent only briefly described and illustrated a small iontophoretic patch to be placed on the inferior conjunctiva and sclera.

In U.S. Pat. No. 6,154,671, Perel and Behar described ocular iontophoretic devices containing various annular medicament reservoirs basically at the limbus and limbal scleral and with little contact with more posterior sclera. Return electrode placement in relation to the active electrode in one embodiment, the menicus flat device, does not favor the driving of medications into the eye because the resultant current travelling between these two electrodes is significantly above the scleral surface. In other embodiments, the return electrodes complete the circuit by touching the eyelids, again diverting current and iontophoresis to the eyelids and away from the eye. Barriers to prevent unwanted diffusion of medications are not well described.

Scleral inserts in an annular shape have been described by Roy in US Patent 2006/0142706. These polymer scleral inserts have medicament reservoirs to release medicament through the microporous walls; these inserts are not intergrated with an iontophoresis device. This patent mentions that an iontophoretic device known in the art can be placed in the vicinity of the scleral inserts. This patent further mentions that the inserts can contain electrodes but doesn't described how they could be attached to a doses controller of an iontophoretic device nor how barriers can be constructed to minimize medicament loss.

The sclera and conjunctivae, in contrast to the corneal barrier, are known to be quite permeable to even large biological molecules. A more effective transscleral drug delivery route than what has been previously described is desirable. Maximizing the scleral contact area should be utilized. Iontophoresis can enhance the delivery of charged medicaments across the broader sclera. Hypothermia can potentially enhance medicament delivery by vasoconstriction to prevent unwanted diffusion of medicaments systemically.

With the new technologies now available, it is time for a new approach to controlling the temperature of the CNS and the eye and orbit by doing local cooling from outside surface of the eye without entering the eye surgically. Furthermore, hypothermia intergrated with iontophoresis can offer improved medicament delivery to the eye, optic nerve and orbits. By administering medications via iontophoresis, microneedles or other means to the eye/orbit directly in a continuous fashion coupled with hypothermia, there may be a new approach to treating eye disease. Better designs of electrodes and better placement of medicament reservoirs for ocular iontophoresis are described in this patent.

SUMMARY OF THE INVENTION

The invention provides devices and methods for enhancing the treatment of diseases of the eye and orbital tissues. More specifically, the invention provides devices and methods for controlling the temperature of the eye, optic nerve, orbit, and peri-orbital tissues by applying hypothermia, hyperthermia, or euthermia rapidly without violating the tissue with surgical intervention. Moreover, the devices and methods can also apply medications and/or chemicals to the eye, optic nerve, orbit, and peri-orbital tissues. The device can also be equipped with iontophoretic capabilities, microneedles or other modalities to facilitate the delivery of medicaments. An effective trans-scleral drug delivery route is desirable to avoid more invasive delivery routes. The sclera and conjunctivae, in contrast to the corneal barrier, are quite permeable to even large biological molecules.

Administration of medications to the cornea and anterior segment of the eye is also enhanced by the combination of temperature control and iontophoresis.

The first embodiment of the device comprises a thermal-regulating shell consisting of a multi-layered hemispherical unit that conforms to the shape of the eye, fitting into the fornices of both the upper and the lower eyelids. The medium circulating within the thermal regulating device will usually be a liquid; one or more than one gases can be dissolved or infused into solution to decrease the viscosity of the liquid to improve flow. Fluid will flow into an entry port and out through the exit port. Rapid flow of fluid will result in both convection and conduction exchange of temperature between the device and the surrounding tissues, including the eye and its adnexae. Forced convection of solutions at different temperatures may help mixing of liquids and more effectively exchange heat. At the interface of two different surfaces with different temperatures, natural convection takes place.

Rapid flow of fluid will facilitate the administration of appropriate medications and/or chemicals to the adjacent tissues through a semi-permeable membrane, or nanotubules, or millipore/micropore system, or other appropriate materials that deliver treatment to the tissues. The direct effects of dissolved gases or minute bubbles of gas on lowering liquid viscosity and improving thermal exchange may be an advantage. In addition, oxygen delivery transsclerally may be beneficial in treating various ischemic ocular pathologies and can be added as a useful treatment modality.

In diseases such as central retinal artery occlusion, it is desirable to rapidly lower the temperature within the neurological tissue of the eye to preserve it from ischemic injury. In other diseases such as uveitis, ocular infection, and ocular inflammation a slower flow of fluid may be efficacious.

A pump system may be configured with a peristaltic pump with multiple inlet and outlet connections that have the capability of transporting large volumes of fluid rapidly throughout the entire volume of the thermal-regulating shell, distributing the fluid through channels within the shell. Depending upon flow characteristics, the system may be custom designed for the best delivery of fluid to the tissues of the eye, the orbit, and adjacent sinuses and other peri-orbita. The pump may be battery operated and simplified to allow for portability and ease of use. An external system will control temperature, pressure and flow rate.

The thermal-regulating shell may be designed with an opening in front of the cornea to allow for measurement of intraocular pressure and for viewing the structures within the eye from the cornea to the retina and optic nerve. If the shell is designed without the opening in front of the cornea, then thermoregulation and administration of therapeutics to the anterior segment of the eye may be facilitated.

In order to place the shell around the eye and beneath the eyelids, an inserter will allow for gentle placement of the thermal-regulating shell beneath the lids. The shell will be designed with a semi-firm material such as metal or plastic or other synthetic substance placed into the shell to give shape and firmness. This may be configured in a ribbing pattern or a matrix to keep the shell in contact with the surface of the eye. Once the shell is in position, the inserter is removed, and the shell remains in close contact to the eye.

When treating the posterior orbita including the optic nerve, it may be desirable to surgically open the superior and/or inferior fornices to allow the thermo-regulating shell to enter the orbit more posteriorly, closer to the tissue to be treated.

In the case of central retinal artery occlusion, it may be advantageous to create pulsations with both positive and negative pressure through the dual-layered shell. The pulsations of the shell will generate differential pressures within the eye, allowing for dispersion of the embolus out of the major retinal artery. Eye-pressure measuring devices can be built into the shell to monitor intraocular pressure and regulate the fluids flowing through the shell to prevent excessive pressure on the eye.

By coating the outer surface of the shell with an insulating material such as a ceramic, direction of thermal regulation and delivery of medications can be targeted more toward the eye. By coating the inner surface of the shell with appropriate films, one may direct thermal regulation and delivery of medications to other tissues of the orbit, peri-orbita, and surrounding sinuses.

Medications may more easily penetrate the sclera of the eye resulting in higher levels within the eye. By using the shell, the transscleral route is used as extensively as possible to reach posteriorly with the medicament delivery chambers enveloping around the spherical ocular globe. Near the equator of the eyeball, the sclera is the thinnest, measuring about 0.4 mm; anteriorly, near the limbus, the scleral thickness is about 0.8 mm and posteriorly, near the optic nerve, it is thicker than 1 mm. Therefore the easiest entry of medicaments across the sclera is near the equator. Aside from therapeutic advantages of ocular hypothermia, cooling the eye would constrict the conjunctival vessels and many episcleral vascular and venous plexuses to decrease systemic absorption of medicaments.

Since the shell will be placed behind the equator of the eye, therapy will be directed into the posterior half of the eye including the vitreous, the retina, the choroid, the macula, and the anterior optic nerve. Temperature control will also extend to the posterior half of the eye. In the case of hypothermia, preservation of the neurological tissue of the retina and optic nerve can be achieved despite insult such as ischemia. The physician will have a longer period of time to treat the insult with medical therapy and/or surgery.

The shell delivery systems can combine the beneficial effects of tissue thermal regulation and iontophoresis-assisted penetration of medications and other biochemical agents. A thermal regulating device conforming to the eyeball and eyelids, as herein described, can contain permeable cells/chambers filled with a medicament and can be equipped with an iontophoretic bioelectrode connected to a dose controller device which is battery-operated or which can be powered via an electric outlet. Medications, which are charged or can be charged and delivered iontophoretically, include but are not limited to steroids, non-steroidal anti-inflammatory agents, anti-vascular endothelial growth factors (anti-VEGF), other growth factors, hormones, anti-viral agents, antibiotics, anti-fungal agents, transvection therapeutics, anesthetics and other pharmaceutical agents.

In the case of infections of the anterior segment of the eye, hypothermia and appropriate medical therapy will both halt the progression and destroy the infective agent. Infections within the eye (endophthalmitis) will also respond to hypothermia and appropriate medical therapy, especially with rapid cooling and constant administration of appropriate medical therapy into the eye through the sclera. Rather than giving large doses of systemic antibiotics or other anti-infectious agents, it may be possible to produce effective levels of medication by delivering therapy closer to the site of infection.

There are many advantages of combining hypothermia with iontophoresis. Previous iontophoretic attempts without hypothermia have invariably resulted in ocular burn injury. Hypothermia, in addition to having its own therapeutic benefits, can prevent overheating of tissue from the iontophoresis electrodes and electrical currents. The circulating cooling fluids can carry away the bubbles formed by iontophoresis Selective hypothermia to certain tissue regions can constrict the blood vessels and prevent systemic spread of local medicament. Hypothermia can prevent or delay the onset of tissue edema and injury thus improving the iontophoresis delivery of medicaments. Hypothermia can prevent the inflamatory cascade, slow down cell metabolism and delay or prevent apoptosis of injured cells.

Circulating electrons and ions can create magnetic fields. Conversely, magnetic fields or magnets can drive ions and electrons. Iontophoresis can therefore be initiated by magnetic fields and by magnets. Magnetic polymers shaped to conform to the contour of the eye can drive ions into ocular tissues. This novel approach has not been previously described.

Anesthetics from both the ocular shell and the eyelid speculum-like thermoregulating devices may be delivered more effectively via iontophoresis to the eye, eyelids, orbital and periorbital areas. Preservative-free anesthetic agents can be delivered to the eye non-invasively and effectively to improve on current topical ocular anesthetic techniques.

Preoperative topical application of semi-frozen balanced salt solution (BSS) is currently used by refractive surgeons to reduce pain after epi-LASIK or other refractive procedures. In refractive laser keratomileusis, the corneal epithelial layer is removed for laser ablation on the corneal stromal bed following which this epithelial layer is repositioned over the ablation bed to circumvent some of the disadvantage of surface laser ablation. The rate of frozen BBS application on the pre-operative cornea is about 1 to 2 drops per second for a total of 40 to 50 drops. A more effective way of cooling the eye peri-operatively is to use our device to deliver cold anesthetics to the eye, eyelids and periorbita and to achieve more complete local and regional anesthesia not achievable with topical anesthesia alone and without flooding of the eye with excessive balanced salt solution. This treatment can be effectively continued intra-operatively.

Inflammation of the eye will respond to both hypothermia and appropriate medical therapy. This includes diseases such as anterior and posterior uveitis, retinitis, choroiditis, vasculitis, papillitis, sympathetic ophthalmia, scleritis, episcleritis, vitritis, and other diseases. Since the entire eye can be cooled rapidly, these diseases can be better controlled without damage to the eye.

Inflammation of the orbit, ocular adnexae, and ocular muscles can be better managed by utilizing hypothermia in conjunction with appropriate anti-inflammatory medications such as steroids, non-steroidal anti-inflammatory drugs, and antimetabolites. Such inflammatory diseases may include Graves' eye disease with exopthalmous and pseudotumor of the orbit.

Infections of the orbit may be amenable to hypothermia and appropriate medical therapy. Shielding the eye from such therapy may be accomplished by coating the surface of the shell that abuts the eye with an insulator such as a ceramic compound. In this way, therapy can be directed away from the eye, toward the infection in the orbit.

Tumors of the eye may be amenable to both hypothermia and hyperthermia. Hypothermia may be an adjunct to presurgical treatment, surgical therapy, and post-operative management. Hyperthermia may be helpful in augmenting the effect of laser therapy, photodynamic therapy, and medical therapy.

Macular disease may respond to a combination of medical therapy, laser therapy, and hypothermia. Preservation of retinal tissue and the prevention of edema of the macula before and/or after laser therapy may be accomplished with this system of thermal control and drug delivery. Age-related macular degeneration can be complicated by subretinal neovascular membrane formation leading to subretinal fluid, subretinal hemorrhage and eventually macular scarring.

Steroid, anti-angiogenic factors such as anti-VEGF, monoclonal antibodies and other biologic factors have been used to suppress neovascularization. The current method of anti-angiogenic administration is intra-vitreal injection which is invasive and puts the eye at risk for enophthalmitis, retinal detachment and scarring. Current medications commercially available for intravitreal injection include Macugen, Lucentis, Avastin, steroids and others. A better delivery technique is needed. The shell combined hypothermia-iontophoresis medicament delivery system can effectively deliver medications into the eye to reach the retina.

In patients who have surgery on the back or neck, they are in a prone position resulting in congestion of the orbit, poor venous drainage, and occasionally blindness. A new approach to prevention of ischemic optic neuropathy following such surgical intervention can be accomplished by using a method of pumping tissue fluid and venous drainage from the orbit to the cavernous sinus.

Not until herein described, there was no device that completely conforms to the unique shape of the ocular globe. Our proposed ocular shell and eyelid-conforming thermoregulation and drug-delivery devices when equipped with ionotophoretic capabilities via electric fields or magnetic field are in a unique position to allow effective contact, maximal delivery and effective therapeutic influence of medicaments on the eyeball, eyelid, orbital tissues and periorbital tissues.

BRIEF DESCRIPTION OF DRAWINGS

FIG. 2 represents a frontal view of a thermal regulating shell with entry and exit ports when it is positioned onto the eye;

FIG. 3 depicts the side view of the thermal-regulating shell when conformed to the shape of the eye;

FIG. 4 displays the side view of the shell placed over the surface of the eye, beneath the lids, and into the upper and lower fornices, a meshwork may be used for structural support and for connecting sensing devices to the eye;

FIGS. 34 and 34*a* illustrate magnetizing the shell shown in FIG. 32 with an external magnet;

DETAILED DESCRIPTION

Figure 1:
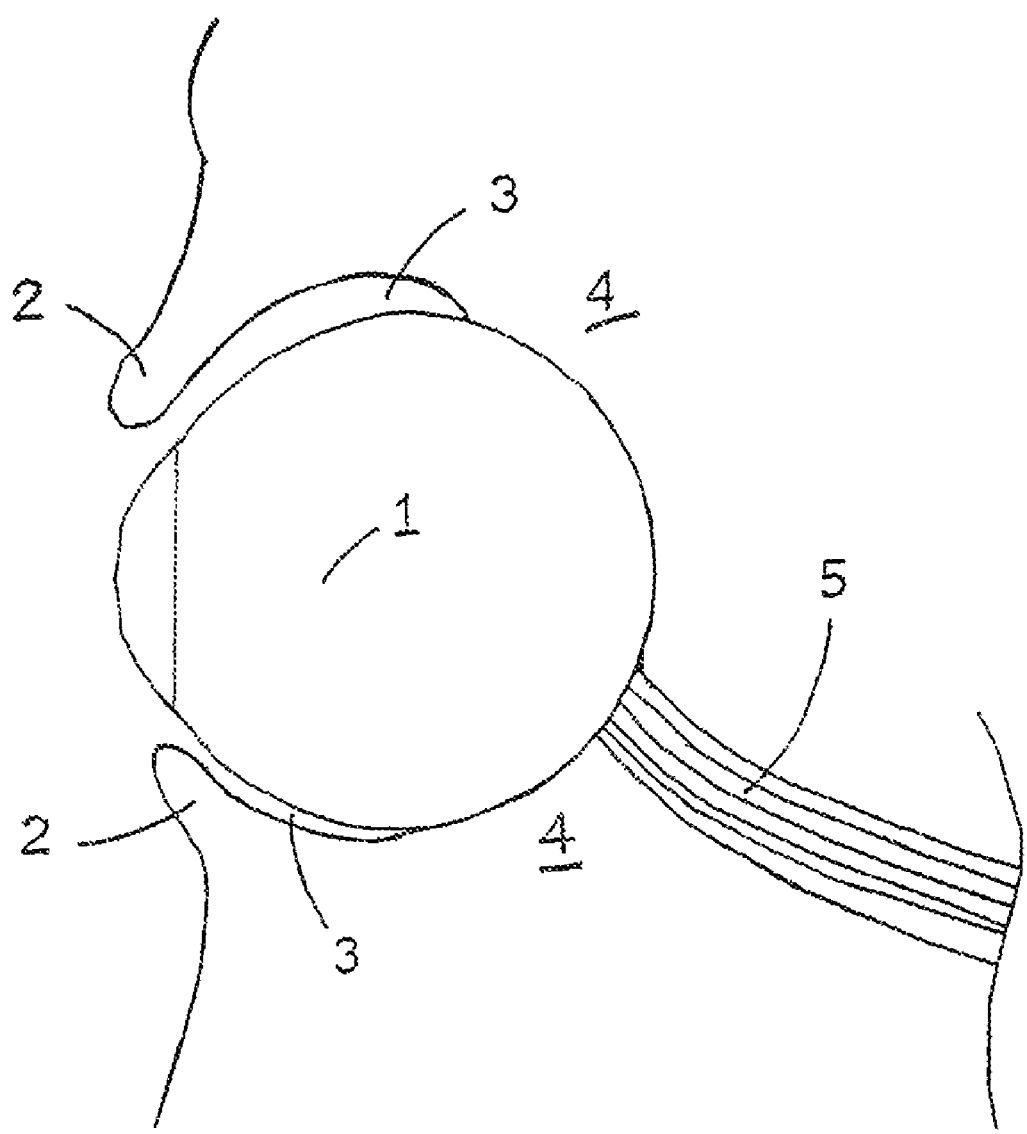
FIG. 1 represents a side view of the eye, eyelids, optic nerve, and upper and lower fornices.
Figure 5:
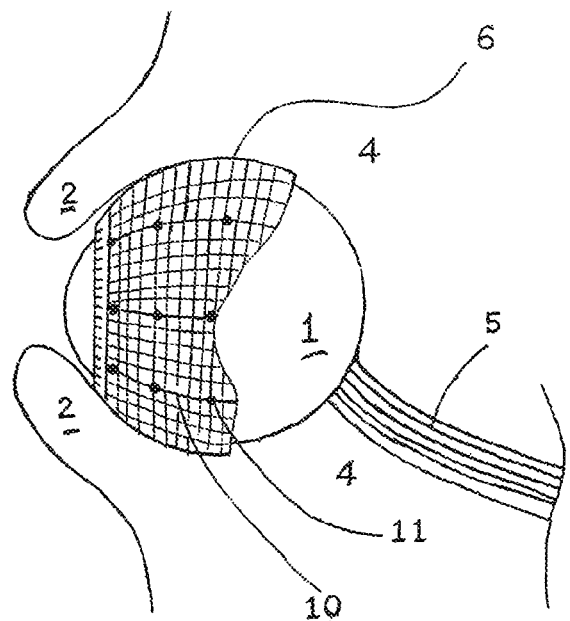
FIG. 5 displays the side view of the shell over the surface of the eye with the integration of a wire-mesh structure onto the shell for support and embedded sensors for data collections points, and stereotatic coordinates for localization of instrumentation and placement of drug delivery, radiation or other treatment means.

In FIG. 1, the normal anatomy is shown of a side view of an eye 1, with upper and lower eyelids 2, upper and lower fornices 3, orbit 4 and optic nerve 5.

A thermal-regulating shell, or device, 6 in accordance with the present invention is illustrated in FIG. 2 (front view) and FIG. 3 (side view). As seen in FIG. 3 the cross-sectional view of the thermal-regulating shell 6 supports a posterior opening 12 suitable in size to allow the shell 6 to conform and slip over the eye 1.

FIG. 4 shows the general position of the device 6 when positioned onto the eye 1. The thermal-regulating shell 6 comprises a fluid cavity suitably designed to facilitate temperature controlled fluid to be circulated within the thermal-regulating shell 6.

The thermal-regulating shell 6 may include a suitably designed central anterior opening 7, a fluid entry port 8, and a fluid exit port 9, both in fluid communication with the shell 6. Other structures such as wires 10 or other suitable semi-rigid means, seen most clearly in FIG. 4, may be incorporated into the thermal-regulating shell 6 which can facilitate fluid flow within the shell 6. This provides a supporting structure as well as a method to direct fluid evenly or preferentially for improved thermal transfer between the eye 1 to the thermal regulating shell 6.

Figure 6:
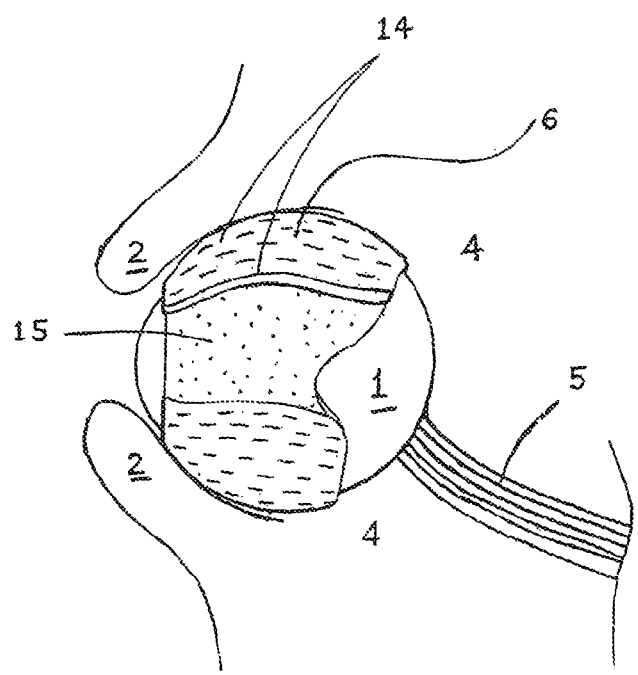
FIG. 6 represents the side view of the shell with the shell lumen inner system partially exposed, where a substance such as a medicament can be administered to the eye through its semi-permeable inner shell membrane or to the orbital tissue through its semi-permeable outer shell membrane and its peripheral tissues.

In FIG. 6, medicament or other fluids will pass through its semi-permeable membrane to the eye 1 and/or surrounding orbital 4 tissues. Microtubules 13, nanotubules, micropores or other transport system will deliver this medicament through its inner semi-permeable membrane 15 and/or outer semi-permeable 14 layer.

Previous iontophoretic attempts have invariably resulted in tissue burn.

Figure 7:
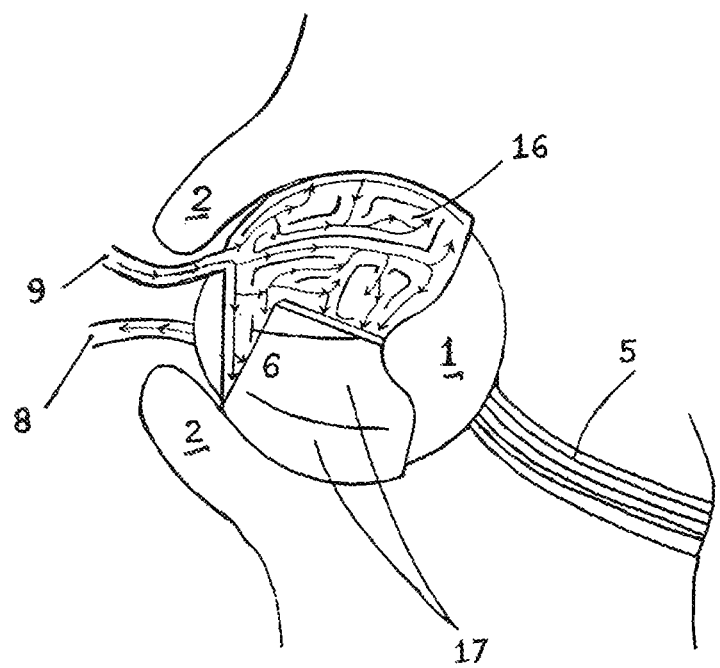
FIG. 7 displays the side view of the shell with the shell lumen partially exposed, showing the inner fluid channels and cavities exposed below its outer layer.
Figure 8:
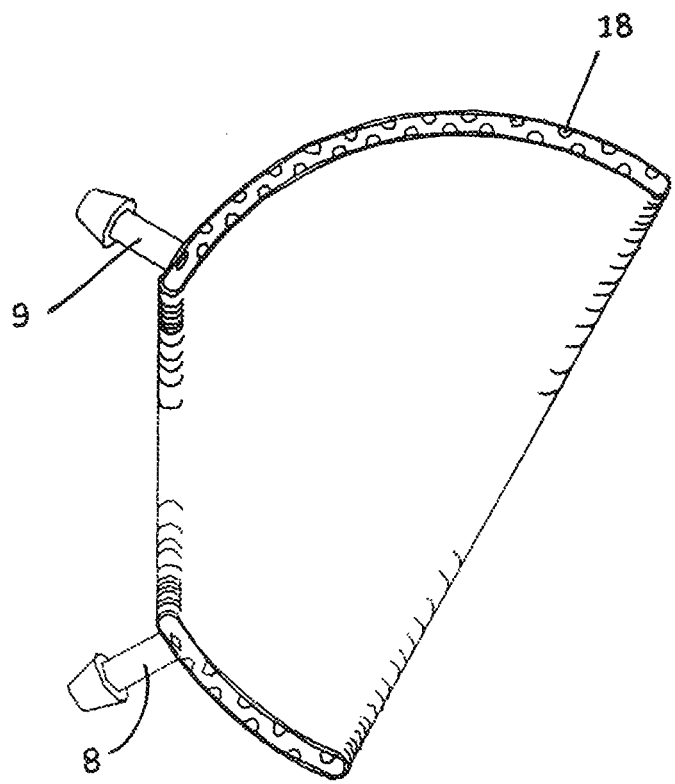
FIG. 8 depicts the sectional view of the shell with its channels and ridges within the shell lumen.

Within the inner system of the shell in FIG. 7, there are cavities 17 where fluid flows through its channels 16 to optimize thermal transmission. This system of channels and cavities throughout the shell are shown in FIG. 7 side view and FIG. 10's section view. The channels are formed by ridges 18 best seen in FIG. 8.

Figure 9:
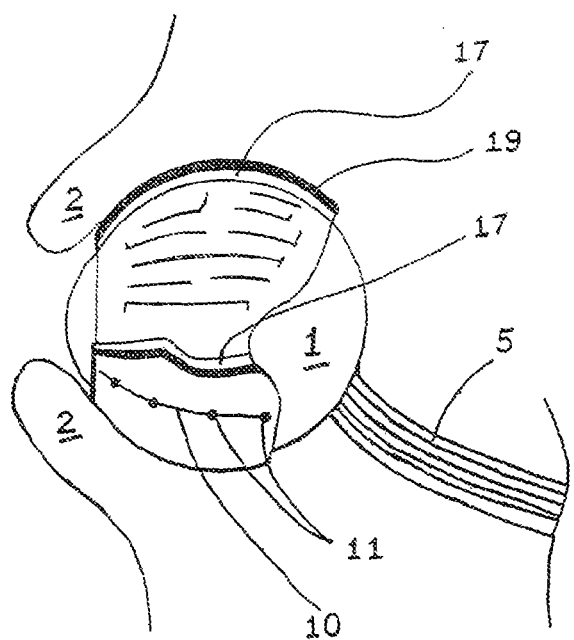
FIG. 9 provides a side view of the plural layer shell with a more rigid structure such as ceramic insulation or lead shielding on its outer layer.
Figure 10:
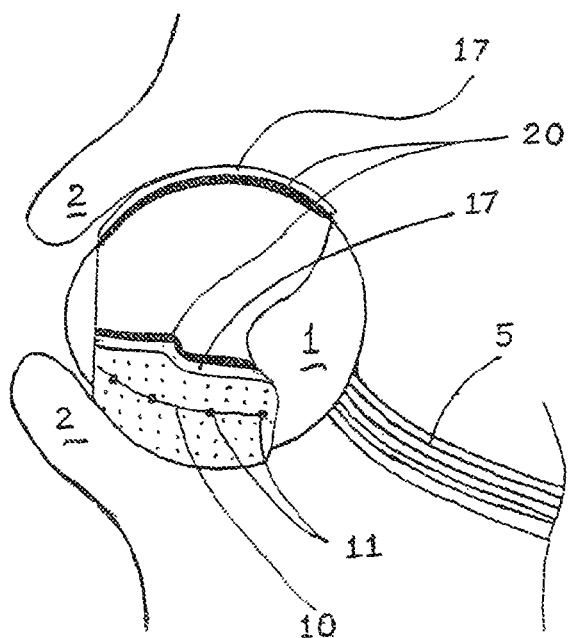
FIG. 10 shows a side view of the plural layer shell with a more rigid structure such as ceramic insulation or lead shielding for its inner layer.

The plural cavity shell may contain a rigid outer layer or cavity 17 shown in FIG. 9 or a rigid inner layer or cavity 17 shown in FIG. 10. This rigid or semi-rigid layer or cavity not only maintains the structural shape of the device, but it can also serve as an insulator composed of a material such as ceramics or act as a shield comprised of a material such as lead covers and may provide other protective purposes.

The system contains a plural cavity shell with a rigid material made of either ceramic, lead, steal, or other rigid substance, and it is located on its outer layer 19 or inner layer 20.

Figure 11:
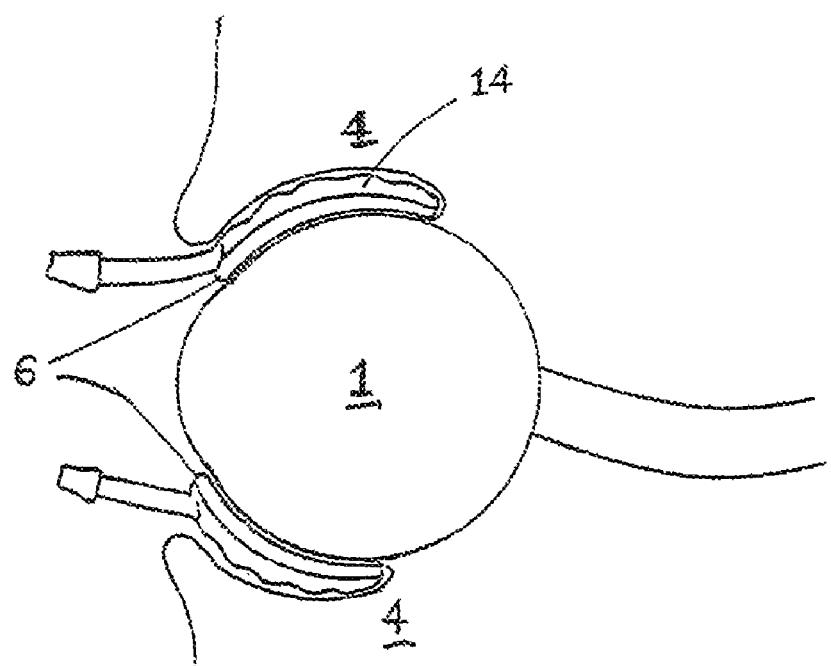
FIG. 11 illustrates the shell with a soft pulsating outer shell wall creating a massaging mechanism for on its outer layer.
Figure 12:
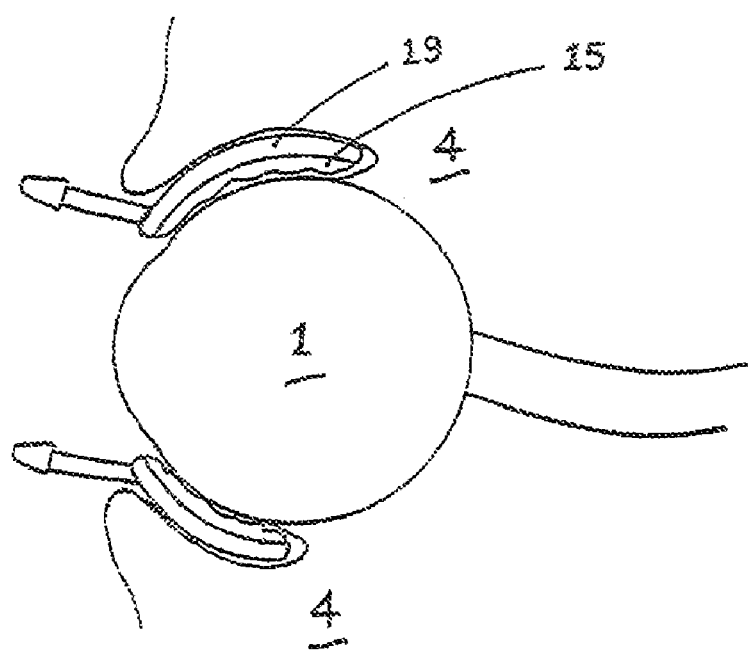
FIG. 12 illustrates the shell with a soft pulsating inner shell wall creating a massaging mechanism on for its inner layer.

In another embodiment, the outer cavity 14 of the silicone rubber shell 6 in FIG. 11 is flexible and pulsating due to an attached pump mechanism that rhythmically raises and lowers the pump speed and pressure. This manually massages the orbital tissue to facilitate venous and fluid drainage to the cavernous sinus and prevents congestion of the orbit. This action may be useful in the treatment of acute ischemic optic neuropathy or in the prevention of ischemic optic neuropathy during prolonged back or neck surgery In another embodiment the firm outer shell layer or cavity 19 shown in FIG. 12 stabilizes the orbit while the inner pulsating shell layers 15 massage the eye 1 to lower the intra-ocular pressure and facilitate intra-ocular vascular flow.

As seen in FIG. 4 the cross-sectional view of the thermal-regulating shell 6 supports a posterior opening 12 suitable in size to allow the shell 6 to conform and slip over the eye 1.

Figure 13:
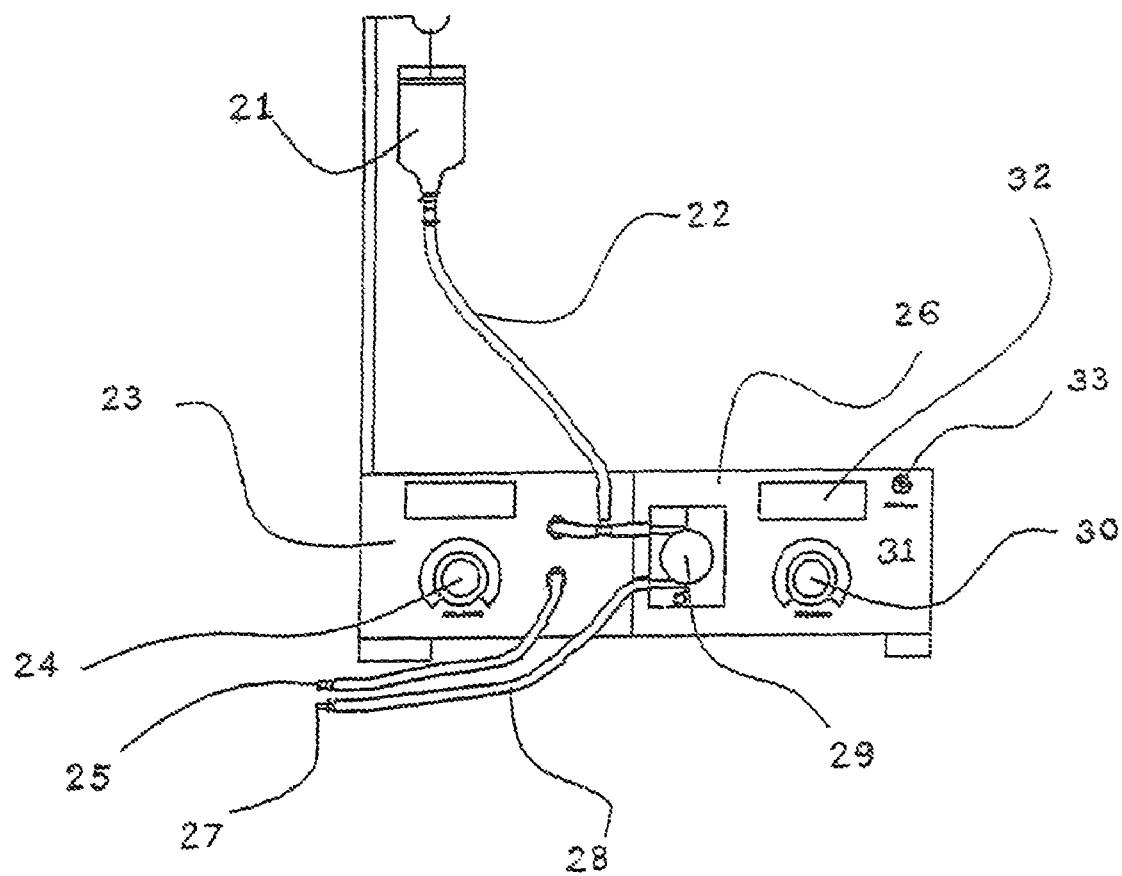
FIG. 13 displays the apparatus for controlling fluid temperature, pressure, rate of flow, flow pulsation in order to circulate temperature controlled and pressure controlled fluid to and from the shell.
Figure 14:
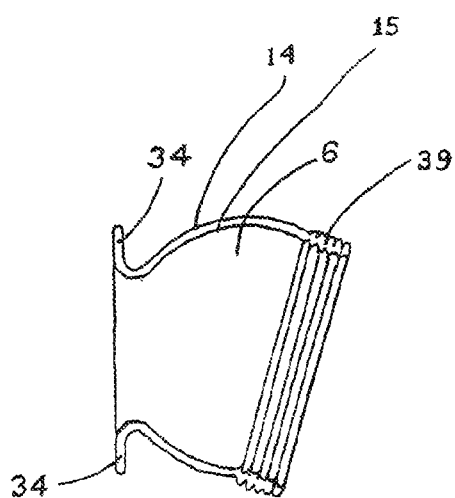
FIG. 14 illustrates a thermal-regulating shell with an eyelid speculum incorporated therein and a compressed posterior shell extension.

As shown in FIG. 13 fluid temperature and fluid circulation can be controlled to predetermined temperatures and rates of fluid flow. Positive pressure is controlled by raising and lowering a fluid bottle 21 height. Fluid pressure is communicated through a fluid tube 22.

Fluid flow is then presented to a temperature control unit 23. Fluid temperature is adjusted to the desired setting by means of the temperature control selector 24. Temperature conditioned fluid is then provided to the supply connector 25 as seen in FIG. 13. Return fluid is presented to the fluid management unit 26 by means of the fluid return connector 27. Using a suitable fluid path tube 28 fluid is pulled from the fluid return connector 27 by means of a fluid pump 29.

Fluid flow is controlled throughout the fluid management system 26 by adjusting the fluid pump speed. Speed selection is adjusted by means of a speed selector 30 which is displayed on the front panel 31 of the fluid management system 26 using a suitable pump speed indicator 32. The fluid management is preferably powered electrically with input power controlled by a suitable power switch 33.

Figure 15:
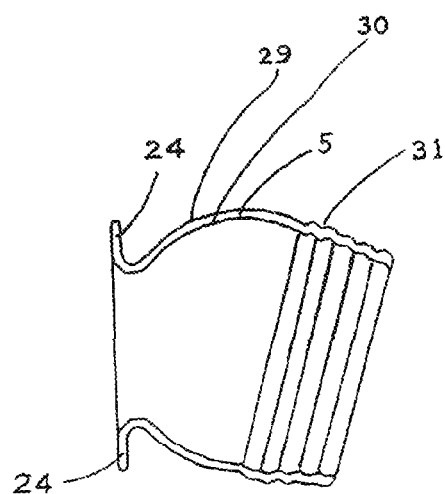
FIG. 15 represents the thermal-regulating shell with the posterior extension extended by positive fluid pressure.
Figure 16:
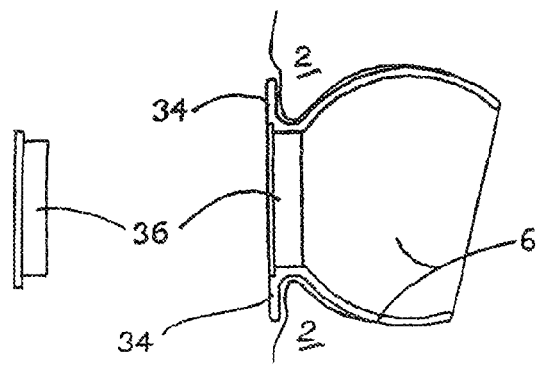
FIG. 16 shows a side-view cross-section of the thermal-regulating shell with a built-in lid speculum in order to restrain the eyelids with and a means to fixate other diagnostic and treatment instruments over the eye.
Figure 17:
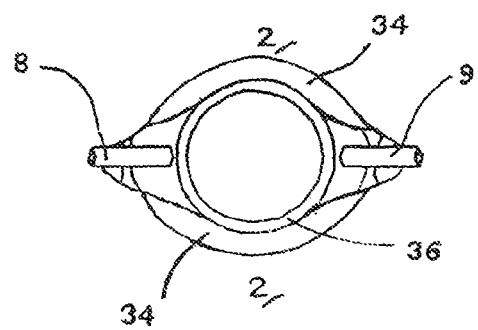
FIG. 17 provides a front view of the thermal-regulating shell having the fluid ports entering and exiting the shell; with the lids held open by the built-in lid speculum placed superiorly and inferiorly, the shell being placed in the superior and inferior fornices and around the eye.

Another means for retaining the thermal-regulating shell 6 is demonstrated using the eyelids 2 which fixate and conform to an eye speculum 34 as shown in FIGS. 6 and 7. The compressed posterior extension 35 is also shown in FIG. 6. The shell 6 conforms to the eye 1 and can be expanded posteriorly by unfolding its posterior extension 35, as shown in FIG. 15. The speculum 34 may be integrated into the thermal-regulating shell's geometry 6. The speculum 34 geometry may also incorporate suitable rigid or semi-rigid geometry to facilitate attachment of other instruments (not shown). As shown in FIGS. 16 and 17, a preferred counterbore fixation ring 36 may be incorporated into and around the speculum geometry 34.

Figure 18:
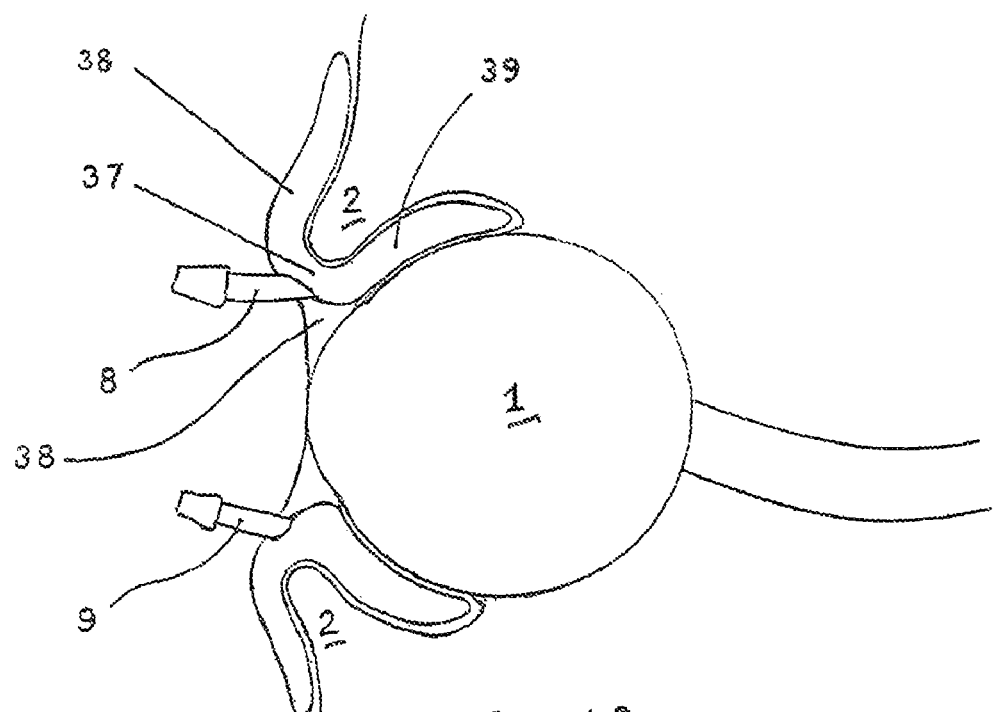
FIG. 18 displays the side view of the thermal-regulating plural layer lid speculum where part of the device is tucked under the eyelids with thermal-regulating shell-like posterior extension over the eye.

In a preferred embodiment, a thermal regulating device having the shape of a plural layer lid speculum 37 is shown in FIG. 18. Its anterior portion 38 cools the eyelids while its posterior portion 39 hooks under the lid to serve as a lid speculum 37 as well as a thermal-regulating apparatus for both the lid and the eye.

Figure 19:
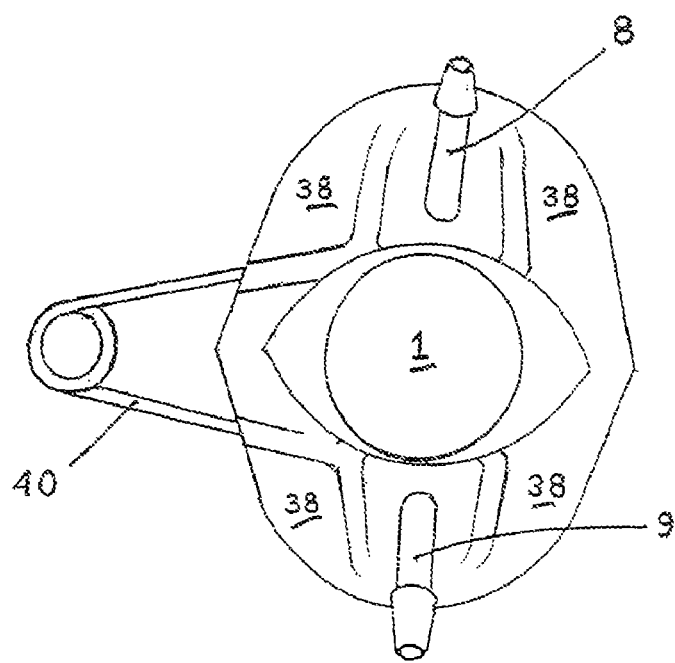
FIG. 19 represents the frontal view of the thermal-regulating lid speculum with underlying posterior shell extension and an inserting clamp attached.
Figure 20:
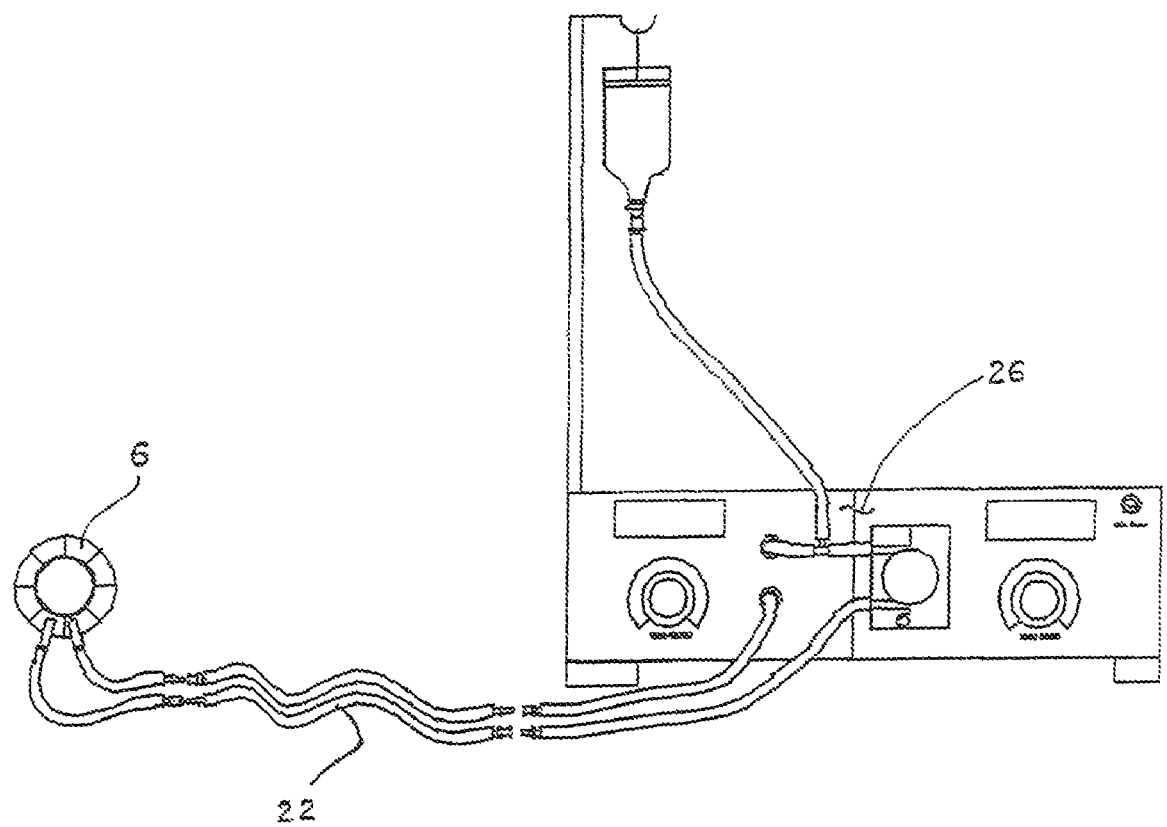
FIG. 20 depicts a system configuration including a fluid management system, thermal-regulating shell and related fluid tubing.

FIG. 19 shows the frontal view of the thermal-regulating lid speculum with its anterior portion 38 visible and its posterior portion 39 functioning as a shell extension hidden from view and an inserting clamp 40 attached;

In FIG. 20 the fluid management system 26 is communicated to the thermal-regulating shell 6 by means of suitable fluid tubing 22.

Figure 21:
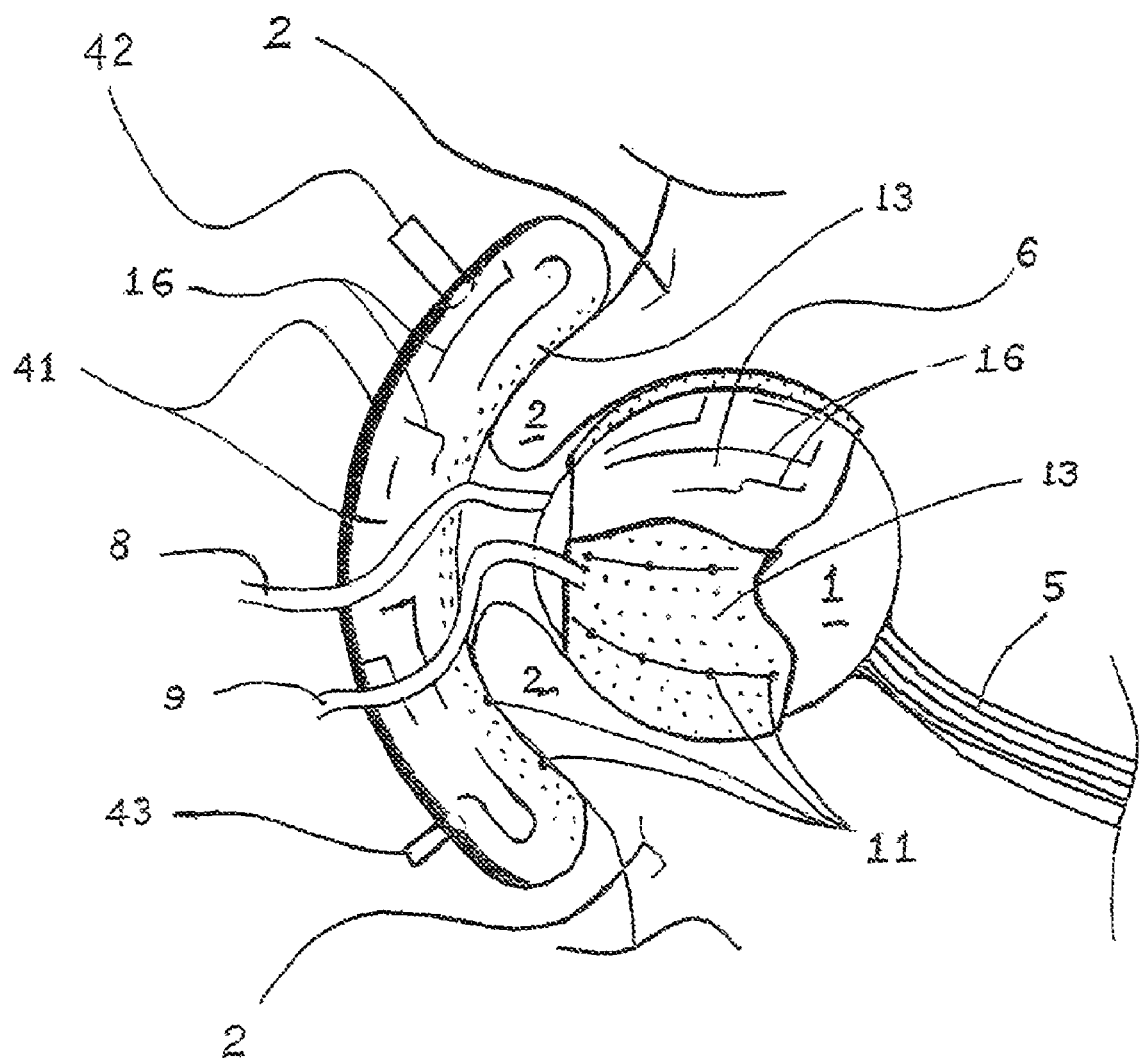
FIG. 21 provides a cross section view of the eye having the thermal-regulating shell installed over the surface of the eye, with a cooling patch disposed over fronts of the partially closed eyelids, each device commanding its own thermal-regulating pump system.
Figure 22:
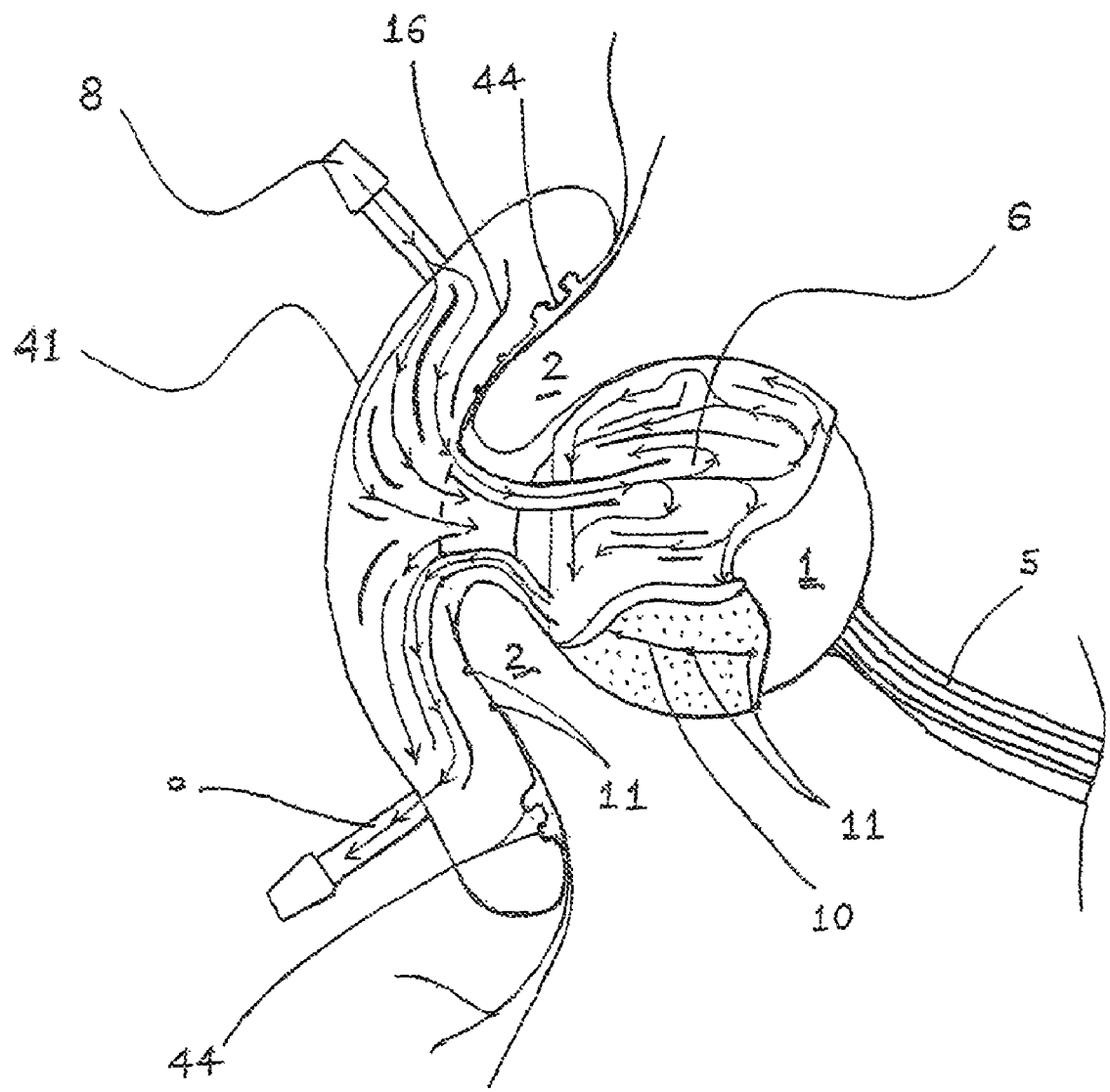
FIG. 22 depicts the cross section view of the eye with an integrated zip-lock system of the patch with the shell and patch sharing the thermal-regulating fluid.

Another means of maintaining thermal-regulating shell 6 placement as well as additional eye cooling can be achieve through the use of a cooling patch 41 with flow channels 16 and separated from the thermal-regulating shell 6 as shown in FIG. 21 or combined with the shell as shown in FIG. 22. Channels 16 are used to encourage fluid flow to the posterior shell in the combined unit.

Figure 23:
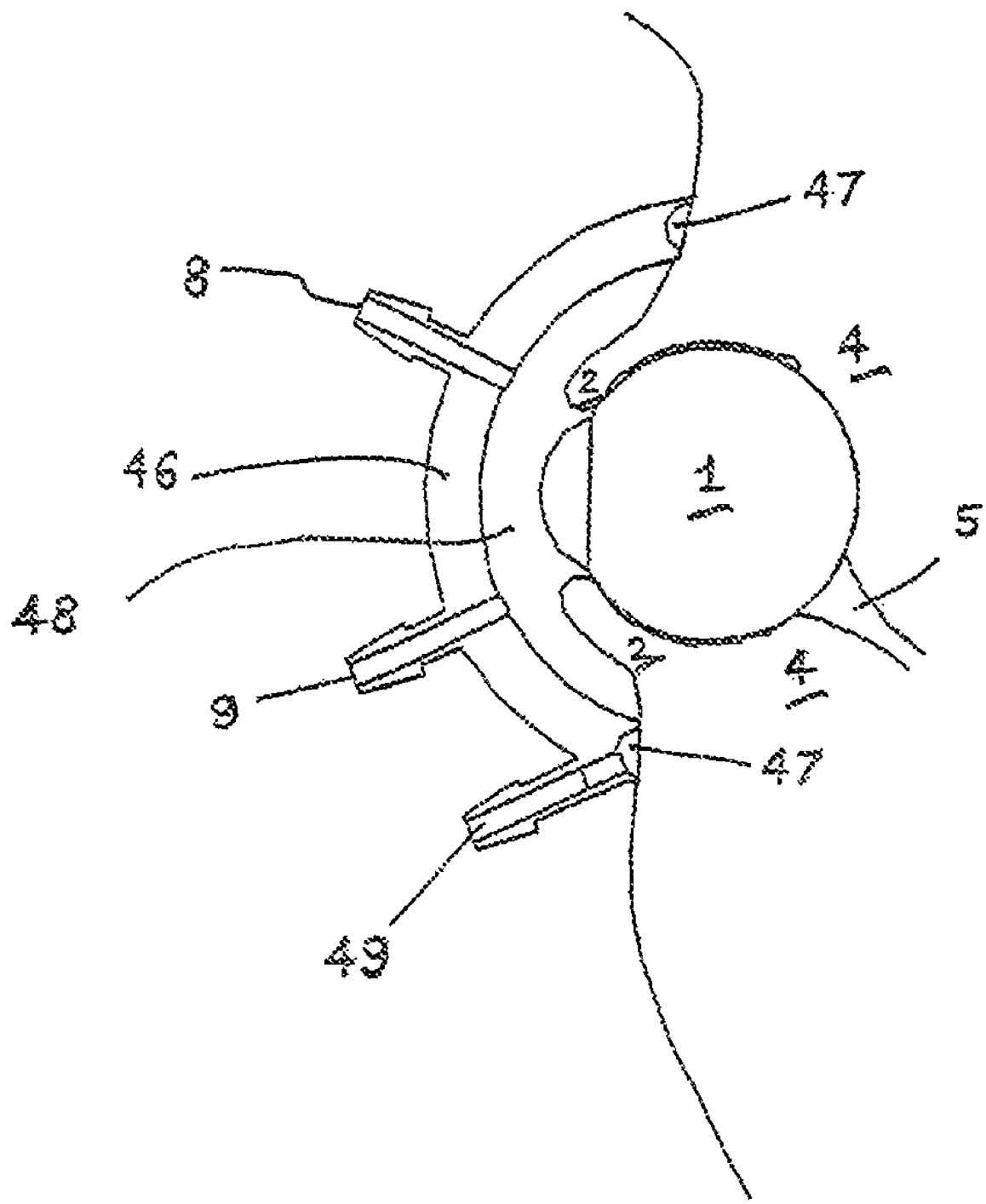
FIG. 23 displays a side view of a suction-aided system for the thermal regulation of the eye, eyelid and peri-orbita.

Another means of maintaining thermal-regulation is the use of the suction aided system 46 that cools the eyelids 2, eye 1, and anterior orbit 4 as shown in FIG. 23.

Figure 24:
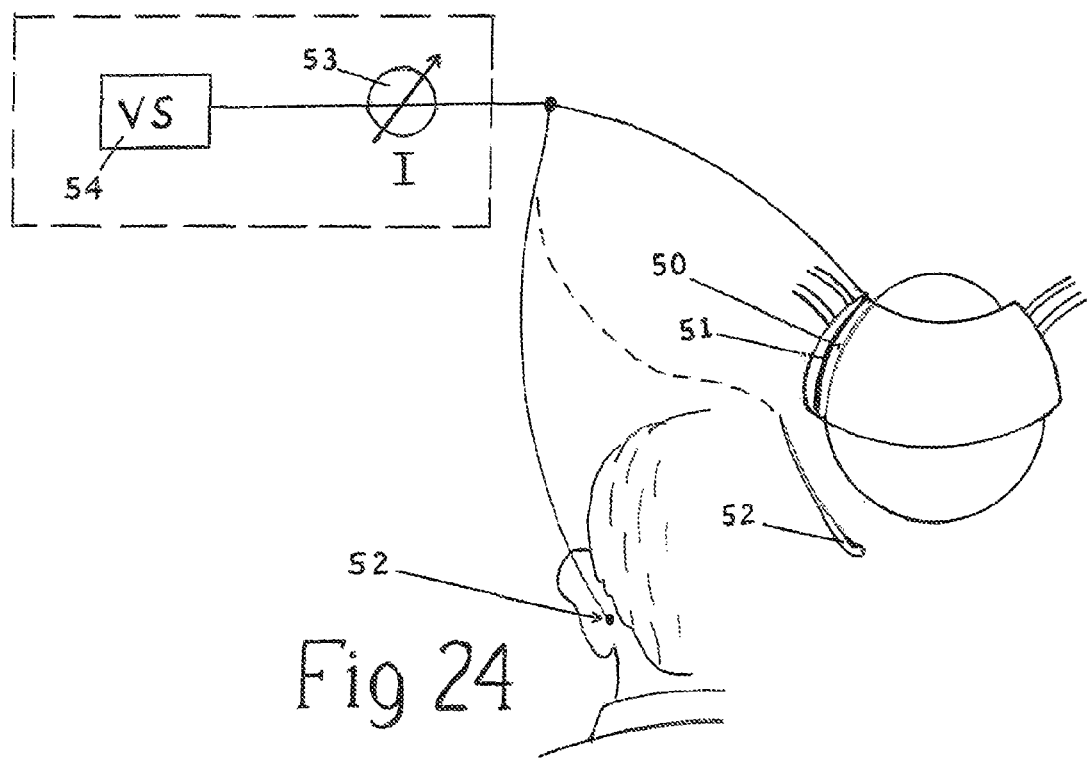
FIG. 24 Depicts an iontophoresis device in accordance with the present invention which generally includes a medicament reservoir containing at least one medicament, an active electrode within the reservoir, a passive electrode across from the biological tissue, a dose controller, and a direct current power source.

The enveloping shell devices for thermal regulation also have tremendous application possibilities in medicament delivery. Their broad surface area of contact with the eye and the generally permeable properties of the sclera, especially equatorially, facilitate medicament transfer. In addition, iontophoresis can drive medications and other slightly charged molecules into the eye. As schematically illustrated in FIG. 24, an iontophoresis device normally consists of a medicament reservoir 50 containing at least one medicament, an active electrode 51 placed within or near the reservoir 50 and a passive electrode 52 placed across from the tissue being treated by iontophoresis. For example, The ground or passive electrode can be placed behind the eye, on the temple, around the orbit or periorbita, behind the head, or preferentially on the posterior side of the eye so that the completed circuit traverses into eye in some way. An electric cable connects the apparatus to a dose controller 53 which is attached to a direct current power source 54. The dose controller 53 regulates the delivery of current and the duration of treatment. The basic set-up for iontophoresis is already familiar to those knowledgeable in the art. The shell's geometries permit broad scleral contact and effective medicament delivery through the permeable sclera which makes this iontophoresis approach unique.

Figure 25:
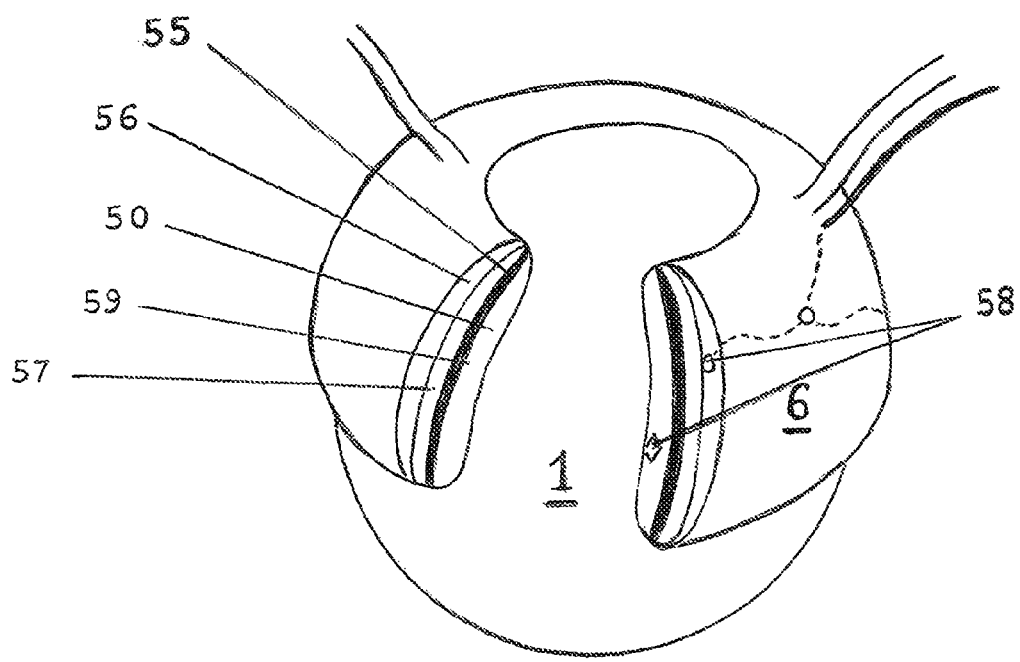
FIG. 25 illustrates a shell with an electrode enveloping around a sclera with an outer surface having an insulator to minimize heat exchange with the eyelids and for preventing physical loss of medicaments to surrounding peri-orbital tissue.

In FIG. 25, a device combining iontophoresis and hypothermia is illustrated. As seen through the cross sectional view of this shell, the electrically conductive framework 55 or mesh embedded within this thermally exchanging shell 6 can be used to create an electric field to propel charged particles into the eye 1 by a process known as iontophoresis. This active electrode 55 is preferentially broad such as a diffuse conductive mesh or framework to spread out the charges and electric field by engaging a broader surface area of medicament delivery as well as to minimize any thermal or electric burns. Preferably, several millimeters should separate the electrode 55 from the eye 1. Hypothermia should eliminate any significant burn. This electrically conductive framework 55 or mesh for iontophoresis can be independent of the network of sensors 58 of various ocular properties; alternatively, it can be interwoven with the thermally regulating network of sensors, structural support, or electronic wires and can share functional, structural and thermal regulating functions. The conductive mesh or electrode materials can be simply thin films of metallic or semi-metallic substances, carbon conductive films or other conductive products, embedded or printed on the shell device. The thickness of the printed film may vary, depending on the material and the desired effects.

The outer chamber 56 of this plural chambered shell functions as a thermal regulator and is usually nonpermeable. The inner chamber 50 contains one or more medicament reservoirs holding one or more medicaments, mixed or separated. The outer wall 59 of this reservoir is in contact with the active surface electrode 55. External to this surface electrode 55 is a medicament barrier 57, preferentially also part of the the inner wall 60 of the outer thermal regulating chamber 56. Other methods of sharing or separating thermal regulation and iontophoretic functions can be designed. These thermally conductive and electrically conductive frameworks may be flexible but strong.

Figure 26:
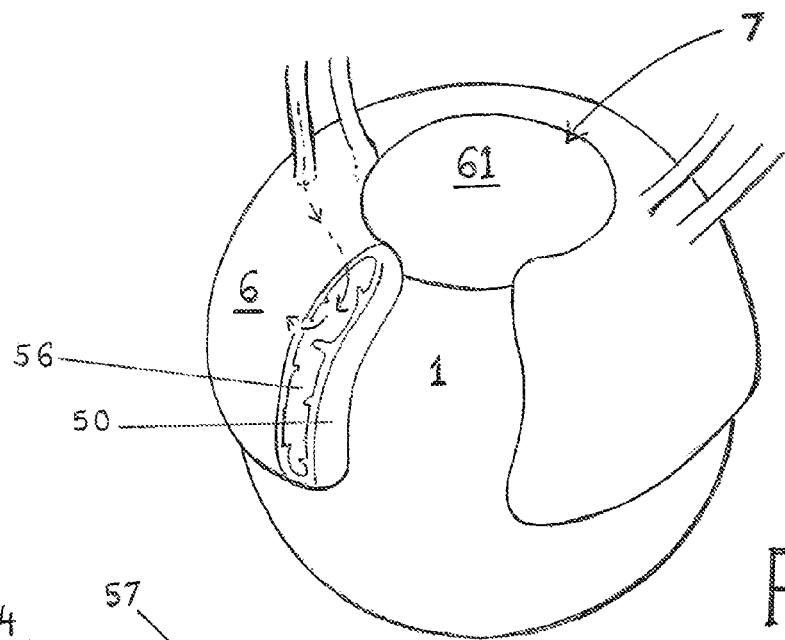
FIG. 26 is a view of shell shown in FIG. 25 partially broken away to show a cross-section with a thermal regulating outer chamber and channels for flow of temperature controlled fluid, along with mesh electrodes for iontophoresis.

FIG. 26 depicts in more details a shell 6 closely enveloping around the sclera of the eye 1 with a central opening 7 for viewing the cornea 61 and underlying structures. Alternatively, the central opening 7 can be closed (not shown). The plural layer shell, as shown in a perspective view in FIG. 26 and from a cross-sectional side view in FIG. 27, has a thermal regulating outer chamber 56 with channels 62 for flow of temperature controlled fluid to enable heat exchange and thermal regulation, and with embedded temperature, pressure and other sensors 58. The outer surface 63 of the outer chamber 56 has an insulator 64 such as ceramic to minimize heat exchange with the eyelids 2, if treatment is aimed at the eyeball 1 and hypothermia is not desired on the eyelids. Besides the regulation of temperature through heat insulation or exchange, this physical barrier 64 can be an extension of the medicament barrier 57 of the inner wall 60 of the outer chamber 56 can prevent physical loss of medicaments (medicament barrier) 57 to the surrounding per-orbital tissue and can be even lightly charged to properly redirect the movement of ionic medicaments.

Figure 27:
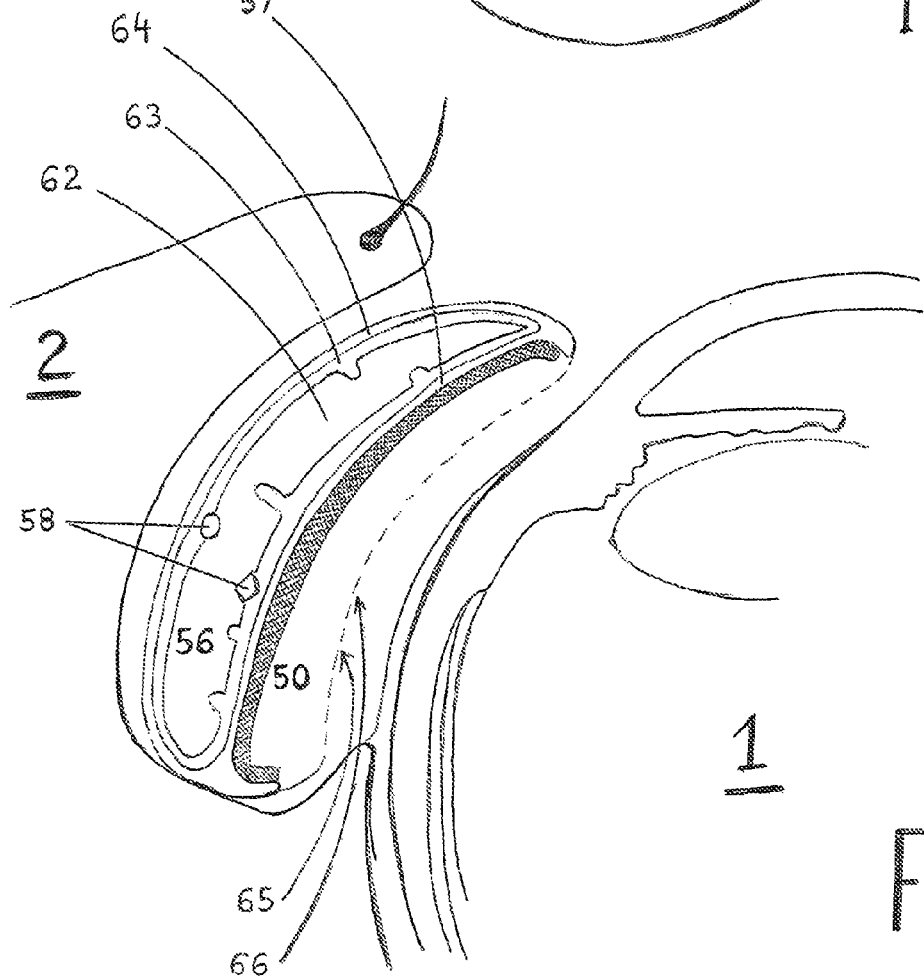
FIG. 27 is an enlarged view of the cross-section shown in FIG. 26.

Also shown in FIGS. 26 and 27, the inner chamber 50 contains medicaments which allow for controlled released of medicaments through the inner millipore membrane 65 (inner wall) 66 of the inner chamber 50. The medicaments can be pre-loaded into a permeable matrix, microchambers, microsphere polymers, microcells or other suitable polymers or sponges contained within the inner chamber. Alternatively, the medicaments can be in solution, gel, impregnated into agar, collagen, mixed in carriers or vehicles, held in porous solids or in other forms contained within the inner chamber. Alternatively, medicaments, alone or mixed in collagen or agar, fast or slow release polymers can be coated onto the inner surface of a single chamber shell, or onto either surface of the inner wall 66 of the inner chamber 50. The carrier media and membrane permeability specifications can control the rate of medicament release.

Figure 28:
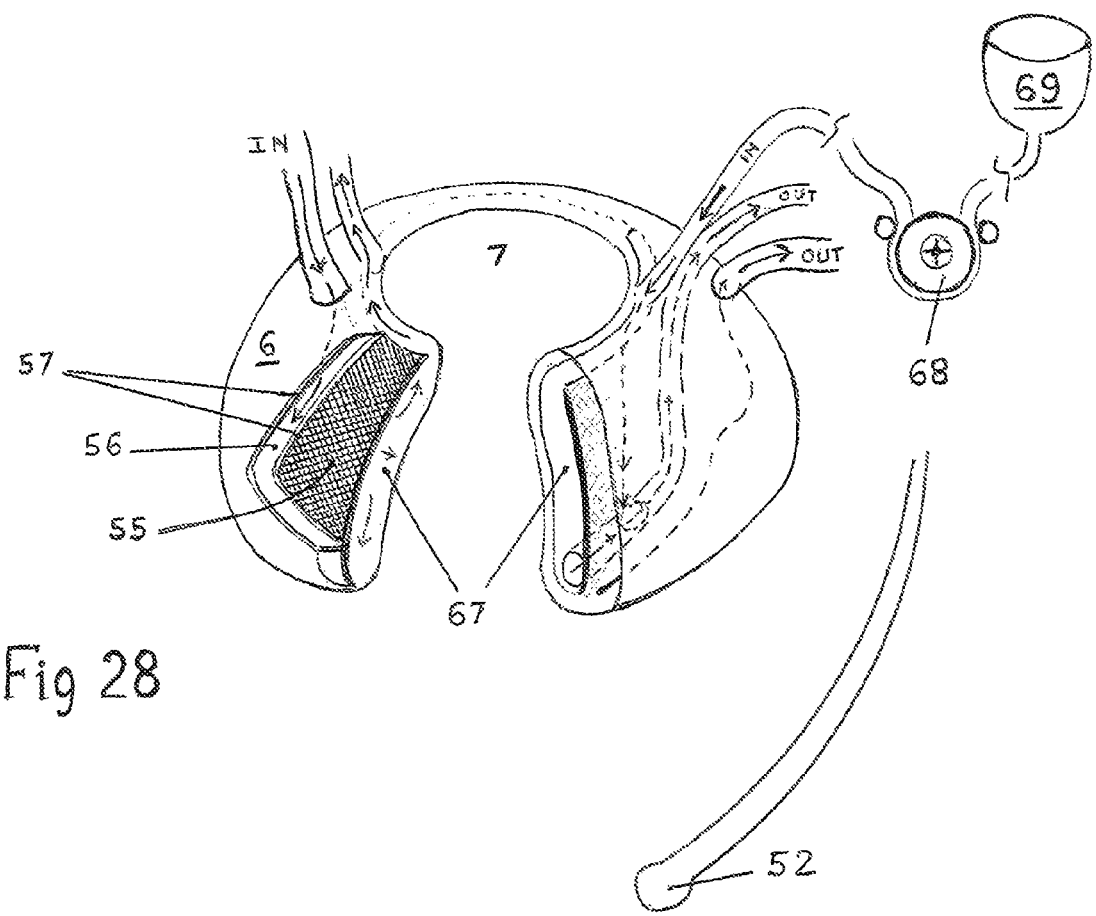
FIG. 28 illustrates driving forces for iontophoresis being provided by magnetic charges; a magnetic lining is disposed external to the medicament chamber with a medicament reservoir being supplied by medicament supply delivered by a pump.

Alternatively, a continuous or a pulsed delivery of circulating medicated solution through one or more inner chambers 67 of the shell device, as illustrated in FIG. 28, appropriately deliver medicaments. A medication pump 68 can circulate the medicated solution from a supply 69 to their proper destinations. Alternatively, gravity can deliver medication to the medicament chamber(s) 67 while a vent or drain can remove excess old solution; the medicament chambers are permeable to ions and molecules. Strategic placement of the medicament chambers, degree of permeability of medicament reservoir walls, concentration of medicaments and rate of medicament delivery regulate the distribution of medicaments. Exchange for fresh medication can help maintain a constant medicinal concentration and pH; one or more external reservoirs can re-supply medicaments to one or more medicament chambers. Various other configurations of medicament placement and delivery in conjunction with thermal regulation can be readily permutated by someone skilled in the art. In general, the ground electrode should be placed as much across the eye on the opposite side of the active electrode as possible. Placement of the two electrodes can significantly influence the efficacy of iontophoresis.

Figure 29:
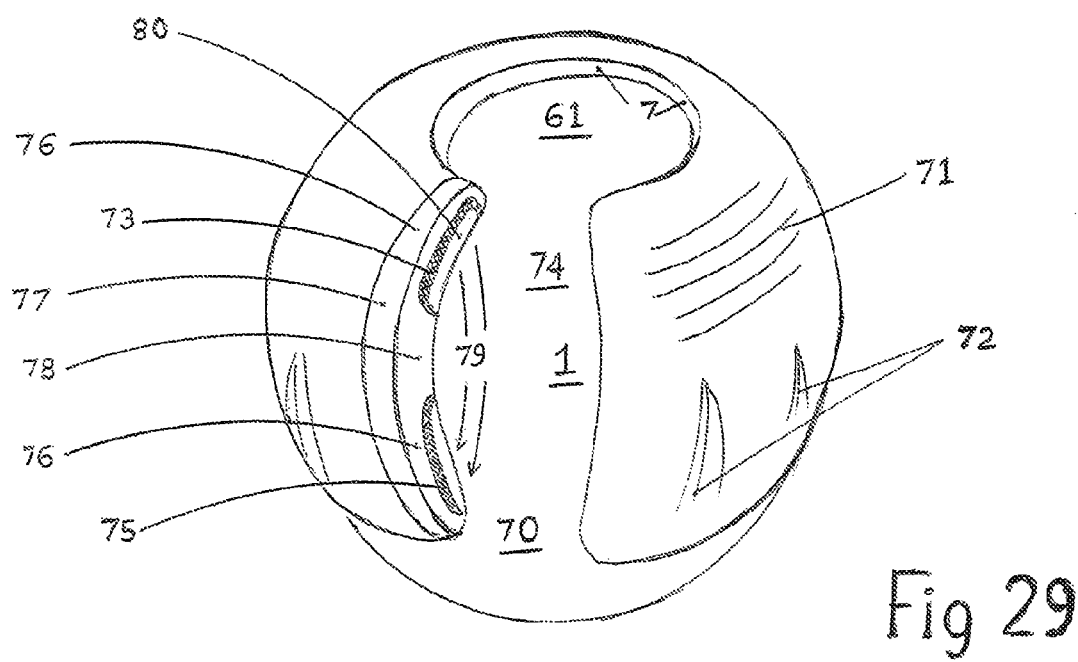
FIG. 29 depicts an expandable shell extending posteriorly, the expandable shell having a anterior treating electrode and a posterior ground electrode.

If a physician prefers to surgically open the conjunctiva, then an expandable shell device can significantly reach the posterior part 70 of the eye 1, as shown in FIG. 29 (perspective with partial cross sectional views). Circular expansion folds 71 can extend the posterior reach of the shell device. Posterior radial folds 72 allow the longer shell to extend posteriorly without undue compression on the globe. In this configuration, the active annular electrode 73 is positioned next to the anterior sclera 74 while the ground annular electrode 75 is placed next to the posterior sclera of the eye 70. The insulating barrier 76 is properly designed to prevent movement of the charged medicaments into the outer chamber 77; the mid barrier 78 placed between the two electrodes 73 75 should prevent direct flow of medicament within the shell. The resultant electric field should favor transcleral movement 79 of charged medicaments from the anterior medicament reservoir 80 into the vitreous cavity of the eye 1 70. Other features described elsewhere in this patent can be incorporated into any this current embodiment.

Figure 30:
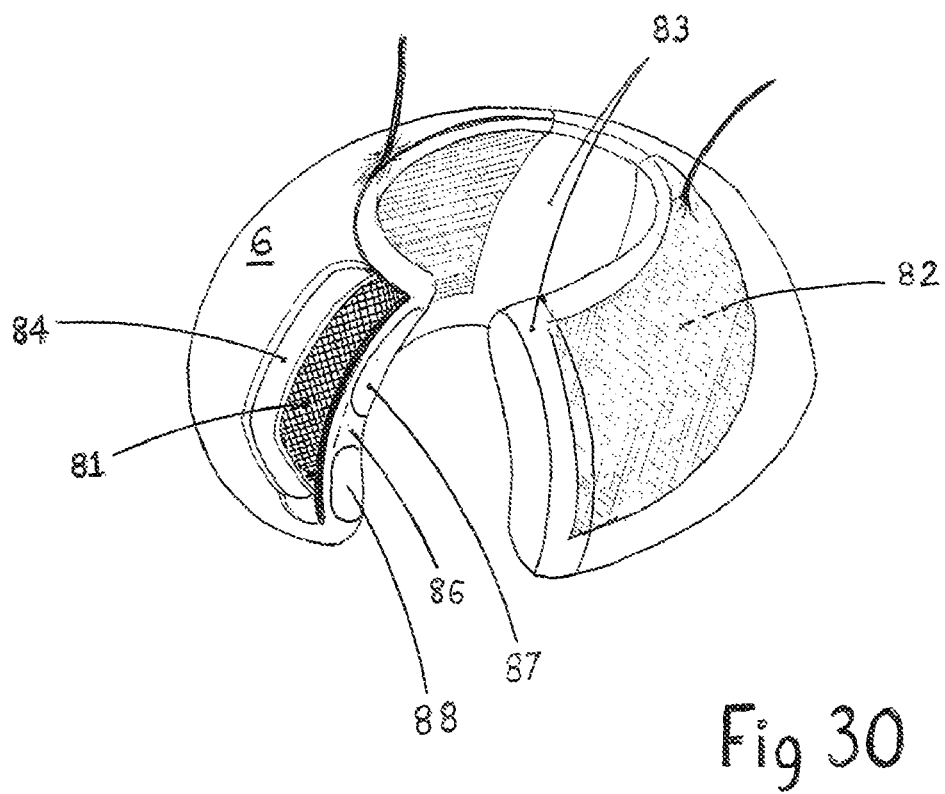
FIG. 30 displays a shell with medication chamber with treating and ground arc electrodes of varying currents within a broad mesh.

In another preferred embodiment, as illustrated in FIG. 30 (perspective and partial cross sectional view), the first electrode 81 consists of a semi-circular conducting mesh-like arc spanning up to the total antero-posterior portion of the shell; circumferentially, it spans usually several or more clock hours on one side of the eye next to the sclera. A similar or dissimilar second electrode 82 of opposite charge and with similar or dissimilar profile serves on the opposite side of the same eye. Preferentially, the treating electrode with adjacent medicament chamber would be broader and larger than the ground or passive electrode. The mesh electrode is exposed to the inner chamber and will preferentially push lightly charged particles towards the eye. Furthermore, insulating barrier bands 83 block electric current from going within the shell favoring instead a trans-scleral path across the vitreous cavity. Thus, the electrical circuit across the eye, through vitreous, bridges the two electrodes while charges traveling along the external conjunctiva and sclera around the eye should be minimal. The secondary route can be minimized by keeping the mesh-like arch electrodes 81 82 shorter therefore increasing the resistance for this flux of current. Furthermore, two non-conducting barriers 83 should take up the potential space between the two electrodes 73 74 to form a mechanical and insulating barrier and minimize any electrical conduction along this path. The outer chamber 84 of the plural layer shell performs thermal regulation. Additionally, to keep the medicaments from external diversion, the outer wall 85 of the inner chamber would preferably be a physical barrier to contain and retain the medicaments. The inner chamber 86 of the shell would consist of various configurations of medicament reservoirs 87; preferably, the charged medicament reservoirs 88 are on the inner side of the electrode of the same charge. It is obvious that any other features of thermal regulation and iontophoresis of the eye, eyelids, orbit and periorbita described elsewhere in this patent may be incorporated into this embodiment.

Figure 31:
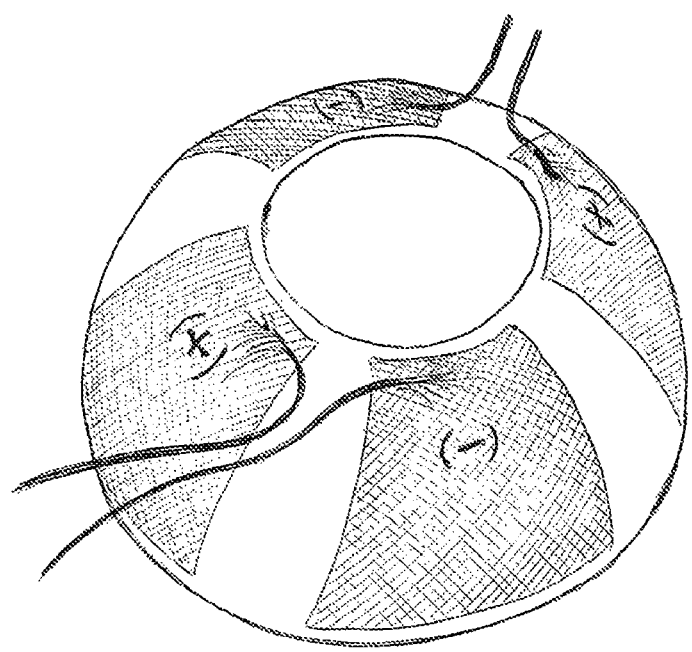
FIG. 31 represents a shell with four mesh-like arc electrodes of alternating charge separated by electrical insulation.

In another embodiment, as shown in FIG. 31, the shell contains four mesh-like arc electrodes 89, 90 of alternating charge separated by electrical insulation. Two electrodes are positive electrodes 89 and two electrodes are negative electrodes 90, positioned in an alternative fashion. Any plural amount of mesh-like arc electrodes, in fact, can be possible. The shell's outer chamber 91 is normally equipped to perform thermal regulation. It is obvious that any other features of thermal regulation and iontophoresis of the eye, eyelids, orbit and periorbita described elsewhere in this patent could be combined with this embodiment.

The conductive mesh design spreads out the electrical charges to prevent localized burn injury of ocular tissues. It is preferably made from a flexible or malleable conductive or semi-conductive material. Various metals and carbon conductive materials can be made into thin films or mesh; some can even be printed, coated or embedded on plastic or polyester surface. The thickness of the printed film may vary depending on the material and the desired effects. The distribution of electrodes and/or mesh-like electrodes will influence the direction, localization and concentration of the delivered medicaments. These can be taylored to specific ocular diseases locallization. The voltage potentials between each and any of the plural electrodes can be set differently to allow for preferential driving of charged medicaments to the intended targets. The amounts and concentrations of medicaments within individual medicament chambers as well as the locations of medicament chambers can be coordinated to maximize the driving of medicaments to the intended targets. It is obvious that various configurations of electrode distributions can be used to maximized the medicament delivery to the intended ocular targets and can be inferred from this presentation. Various embodiments of a combined hypothermia and iontophoresis device would be obvious to those skilled in the art.

Figure 32:
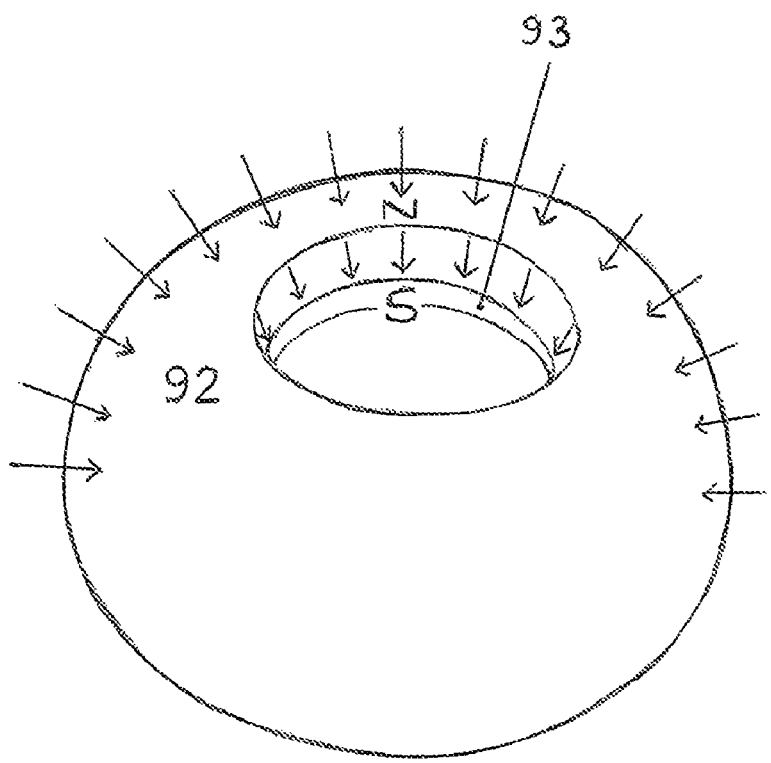
FIG. 32 displays a view of a molded magnetic shell used to propel medication into the eye.
Figure 33:
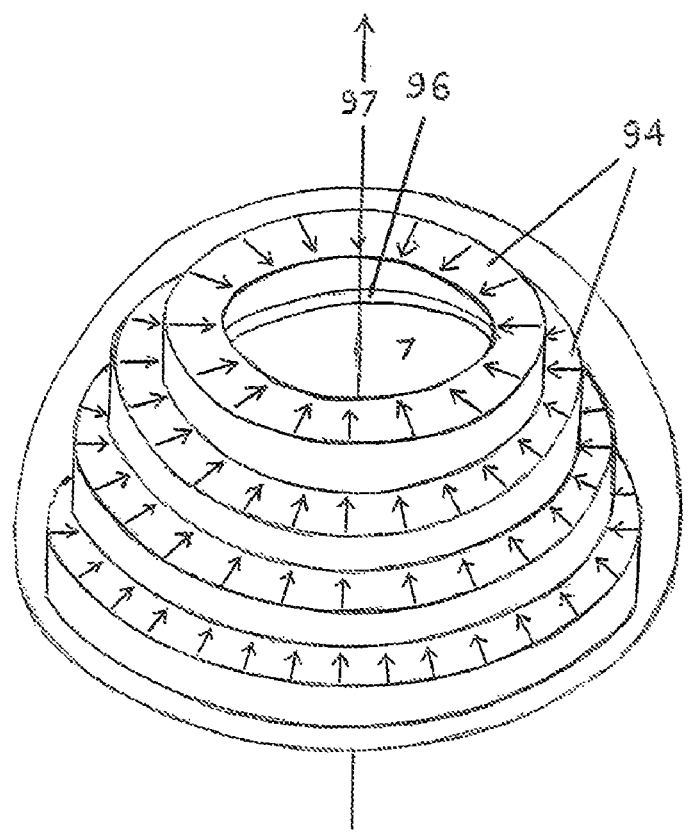
FIG. 33 depicts a magnetic shell with multiple discs and or plates of various size, thickness, and composition.

Instead of electric charges coming from conductive electrodes supplied with direct current, the driving forces for iontophoresis can be by initiated and maintained by magnetic charges. In this embodiment, magnetic fluxes of the magnets, of different strengths and positions, are used to direct and control ionic flow. As shown in FIG. 32, the magnetic shell 92 is external to the medicament chamber 93. Magnets may be incorporated into the shell via several techniques. In a simple design, as shown in FIG. 33, multiple flat discs 94 or plates of various other shapes, with the polarity parallel to their thickness, are embedded in the inner surface of the shell; isotropic ferrite, though weaker, are cheaper and may be magnetized in any direction including "through the thickness T". Rare earth magnets (mainly Samarium Cobalt and Neodymium Iron Boron) can also be magnetized through the thickness "T". Additionally, the unwanted magnetic pole can be insulated by ceramic or other non-conductive materials: barriers 95 are present between these discs as well as on the outer side of these discs to keep the medicaments inside the shell; the medicament chambers 96 are internal to these discs 94 and the polarity of these magnets will drive the medicaments into the eye. Alternatively, as shown in FIG. 33, the magnets can be a series of annular rings 96, with the polarity parallel or radial to their axis 97, aligned in series; in similar fashion to the discs designs, barriers are appropriately placed to favor movement of medicaments into the eye. The device may be a composite of multiple magnets of different sizes and strengths, which preferentially drive charged medicament to intended targets. Thermal regulation cover may be around the external side of the magnetic and iontophoretic device.

The magnet may be a single shell shaped unit 92 (FIG. 32) as technologies exist to make all dipoles aligned in the same direction in more complex shaped molded magnets. For example, bonded magnetic materials can be manufactured inexpensively from magnetic powders bonded in a plastic or rubber matrix. These flexible bonded magnets can be injection molded or compression molded into the shell device or into other unique shapes with finished edges. Magnetic powders can be Alnico alloy (Aluminum, Nickel, cobalt and Iron composite), Rare Earth such as Samarium Cobalt (SmCo) or Neodymium Iron Boron (NdFeB), or Ferrite which all mix well with synthetic plastic or natural rubber binders. The magnetic flux of the molded shell magnet can then be reshaped by strong external magnets 98 to point in the desired direction for maximizing the driving forces of medicament into the eye or any other biological tissue, as illustrated in FIG. 34.

Ceramic magnets made from a ceramic matrix containing Ferrite can be cost effective and can be molded to any shape. Such a magnet can be made into a single shell shaped device after which all dipoles are realigned in the same direction by an external magnets field treatment. In another manufacturing process called sintering, fine powders compacted at high pressure in an aligning magnetic field can be fused under intense heat into a solid shell shape with dipoles all aligned in the same direction. In yet another manufacturing process, Rare Earth magnets can be dye pressed into a shell shape. Casting, extruding and calendering are other methods of manufacturing magnet and are familiar to those skilled in the art. Recently, a plastic non-metallic magnet made from an organic polymer such as PANiCNQ (a combination of emeraldine-based polyaniline [PANi] and tetracyanoquinodimethane [TCNQ]) was created; such organic polymer may be used in iontophoretic applications. Other magnets yet available may be used as well in future iontophoretic applications. Once shaped to the desired form, magnetization of the device can be achieved by exposing the device to properly oriented external magnetic field usually electric current running through appropriately shaped coils 99 (FIG. 34a).

Alternatively, magnets and electric current may be combined to create a stronger electromagnetic force. A current passing through an electrical coil placed around a magnetic device can greatly enhance its electromagnetic flux. Electromagnetic properties of an electromagnetic coil may also be the driving force for iontophoresis of charged biomolecules or charged medicaments in the eye and other biological tissues. Even several simple magnetic rods, with most of the rods shielded and the same polarity aimed at the eye or other biological tissues, can repel similarly charges medicaments into the treating tissues.

The medicament chamber for the above devices can be made with any of the various specifications previously described for iontophoresis with electrical currents. In one preferred embodiment, the medicament is dry coated onto the inner surface of the molded shell magnet. The conjunctiva and sclera can be pre-spiked with microneedles impregnated with medicaments following which iontophoresis with electric currents, magnet or electromagnets can then be initiated. Alternatively, a predetermined amount of medicament can be held in a polymer matrix, collagen or agar coating, or any other vehicles lining the magnetic shell. Alternatively, the eye, eyelid or other biological tissue can be coated with the medicinal gel before application of the magnetic treatment device. These methods and devices are simple, without electric current or wiring, more compact without a dose controller and a power supply box, or battery. Thermal regulation can be combined with iontophoresis via magnets. An additional advantage of hypothermia is that magnets and electromagnetic strengths are normally enhanced when cooled. All adaptations previously described for the shell devices can be incorporated into the magnetic thermal regulation shell designs.

Thermal regulation can also be carried out by Peltier coolers. In this technology, the thermo-electric cooler uses multiple thermocouples in series to achieve a substantial amount of heat transfer. The thermocouples are often made out of a mix of two semiconductors, Bithmuth and Telluride, in which additional impurities are added to alter the amount of available free electrons. The thermocouples are packaged between two ceramic plates or padded with silicon. This is placed partially within the shell or the inner lining of the shell. On the other side of the thermoelectric cooler (TEC), away from the eye, there is a heatsink with proper thermal interface consisting of fins, plates and other means to increase the surface area; a battery powered mini-fan or a circulating body of cold fluids can dissipate the heat from the heatsink. The thermoelectric cooler (TEC) has a wire on each of the two ends; when a voltage is applied to the two wires at the two ends, a temperature gradient is achieved.

Figure 35:
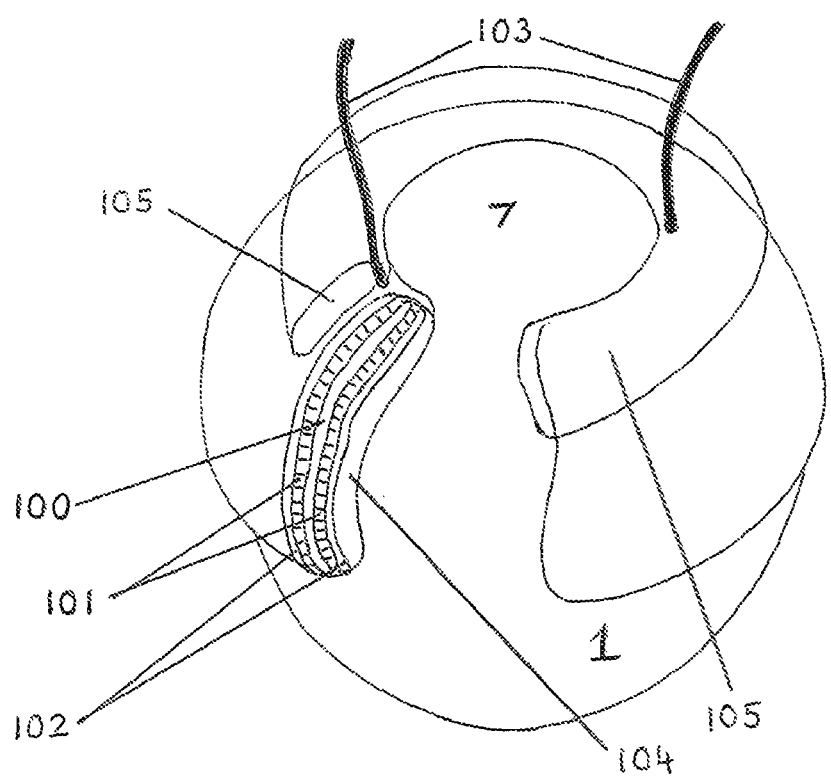
FIG. 35 displays a Peltier cooler attached to the shell device in order to dissipate heat.

In one embodiment, as shown in FIG. 35, the Peltier cooler 100 is shown as embedded to the external side of the shell 6. The thermocouple unit (TCU) with one or more than one thermocouples 101 in series is packaged along the contours of the shell and therefore also conforms to the shape of the eye. The ceramic or silicone packaging 102 around the electrodes can easily be molded into a shell-like unit that can then be incorporated into the shell device. The two wires 103 on each of the two ends of the thermocouples in series are connected to a power source. The voltage difference creates a temperature difference across the two sides of the TCU. As long as certain intraocular sites, such as sclera or ciliary body have acquired a depot of medicaments, subsequent diffusion of such medicaments into other target structures such as retina and maculae can be achieved. An iontophoresis inner shell device 104 can be incorporated into the Peltier device. A heat sink 105 of various geometries can remove the heat Alternatively, segmental placement of Peltier coolers can be used to preferentially direct ions into the eye, or into specific localized segments of the eye using the existing potential differences in the device itself. Alternatively, the iontophoresis process takes place within the inner chamber and the thermoelectric cooling occurs separately in the outer chamber. Those familiar in the art will realize that other designs can allow preferential cooling and ionic movement across or deeper into the eye.

Figure 36:
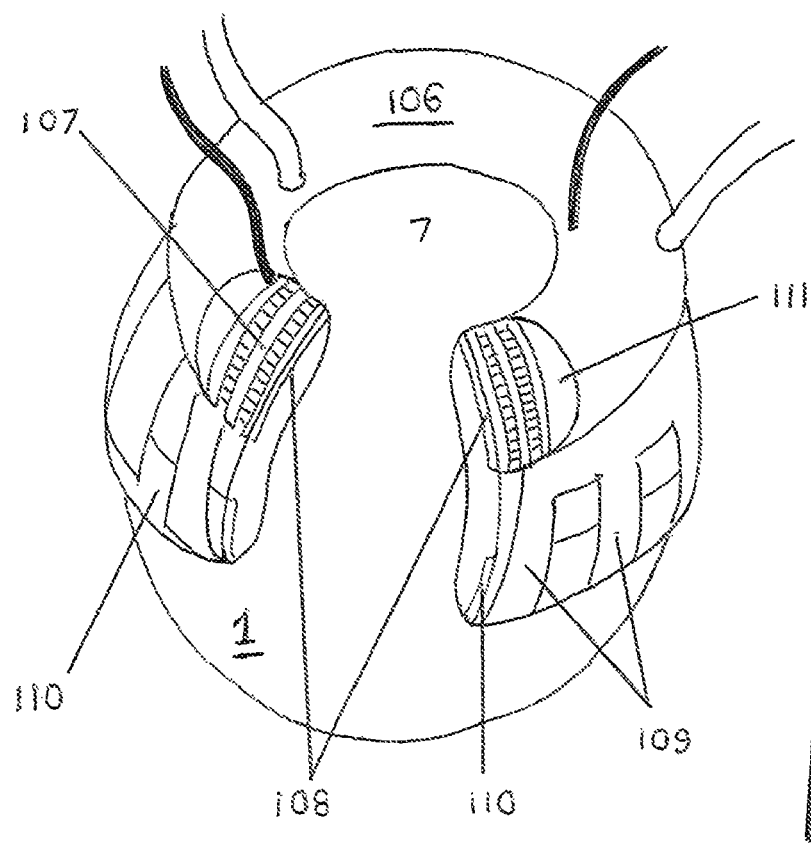
FIG. 36 depicts a Peltier thermoelectric unit that cools the thermally conductive belt.

In another embodiment shown in FIG. 36 the Peltier thermoelectric unit 106 is in less intimate contact with the shell 107 or eye 1 and more indirectly cools the thermally conductive belt 108 which has extensions 109 to the more posterior part of the shell. Heat is drawn from the posterior conductive extensions and posterior annular belt 110 to the anterior annular belt 108. A heat sink 111 is also shown. The Peltier unit can be a composite of multiple Peltier coolers individually controlled to preferentially cool specific parts of the eye and eyelids. The Peltier technology can also be used in the shell-eyelid speculum combined unit to affect thermal regulation of both the eye and eyelids.

The Peltier cooler can function independently as thermal regulating unit. If the geometries are properly configured, the voltage difference between the two electrodes of the thermoelectric device can create a current and promote the movement of ionic biomolecules and serve a second function as an iontophoresis device. Furthermore, in combination with a stand alone iontophoresis unit, the combined Peltier-Iontophoresis unit can have duel modalities.

The thermoelectric unit and the medicament chamber for the above Peltier-iontophoresis device can be made with any of the various specifications previously described for thermal regulation by fluid dynamics. In one preferred embodiment, the medicament is dry coated onto the inner surface of the molded thermoelectric cooler. Alternatively, a predetermined amount of medicament can be held in a polymer matrix, collagen or agar coating, or any other vehicles lining the TEC. Alternatively, the eye, eyelid, or other biological tissue can be coated with the medicinal gel before application of the thermoelectric cooler. A separate iontophoresis inner shell can be incorporated into the Peltier cooler. All adaptations previously described for the shell devices for thermal regulation by fluids, iontophoresis by magnets or currents, can be incorporated into the thermoelectric-iontophoresis shell unit.

Method of Operation

Thermal-regulation of the eye 1 and the surrounding tissues can be used for various therapeutic and interventional purposes. The thermal regulating device 6 uses both conductive and convective methods for temperature control of the eye 1, and the surrounding tissue.

The device 6 may include an anterior central opening 7 to allow for direct inspection of the cornea and other ocular structures when the device 6 is installed on the eye 1. Alternatively, the shell 6 may have no central opening and in this embodiment the cornea, the anterior segment, the eye and nearby tissues can be even more effectively cooled.

Fluid entry ports 8 and fluid exit ports 9 may be placed anywhere on said device 6 though preferentially medially or laterally to take advantage of anatomical relationship of the eye 1 and eyelid 2. There will be a thermal exchange of temperature using conduction between the shell 6 and the eye 1 or other nearby structures and convection of the rapidly moving irrigating fluid.

This device 6 is composed of a material that facilitates heat exchange between the eye 1 and the conductive fluid. A material such as silicone rubber or any other material with properties such as softness, malleability, and good heat-exchange capability is desired.

For purposes of administration of medications and other chemicals, the material may consist of a semi-permeable membrane, or millipore/micropore systems, or microtubules 13, or nanotubules, or material that has been prepared with special channels 16 in its cavities 17 for passage of treatment modalities.

The body of the shell 6 may be reinforced with a wire 10 or other firm mesh resulting in a supporting matrix 10. Various sensors 11 may be embedded in the wire matrix 10 or in the shell 6 in order to take readings throughout the involved tissue surfaces. The embedded sensors 11 can measure various ocular surface properties such as ocular temperature, ocular pressure, ocular surface pH, ionic concentrations, electric charges, electric fields, chemicals detection or concentrations, oxygen saturation, drug concentrations, and other monitoring features yet to be in common use.

The structural frame 10 of the shell 6 can be thermally conductive and attached to a thermal regulating probe (not shown) for the purpose of heat exchange via the circulating fluid, or for direct heat transfer between the thermal conducting frame 10 and the eye 6. This meshwork of conductive and structural material serve as an umbrella-like net that extends the thermo-regulating capability from a concentrated area at the tip of a thermal regulating probe (not shown) to a larger net surface of heat exchange directly with the eye or indirectly with the circulating fluid.

Additionally, depending on the location and distribution of the thermal regulating conductive material, direct heat transfer to the eye, eyelid and periorbita may play an important role as well. Thermally conductive materials may metallic, semi-metallic, non-metallic but thermally conductive or others types of materials. This material preferably is flexible but thermally conductive. Examples of good thermally conductive non-metals include glass, carbon and diamond. This framework can be made of any semi-firm, firm, pliable, malleable or shape-retentive materials with good thermal conductive properties or radiant properties. This framework can be metallic, semi-metallic, polyvinyl, or of other material having memory retention or malleable properties. Fins and plates can increase the thermal conductive surface.

The matrix 10 firmness also assists in pushing the fornices 3 posteriorly and extending the shell 6 coverage to the posterior surface of the eye 1 as shown in FIG. 15. In treatment for the posterior globe or orbit 4, it may be necessary to surgically incise the posterior wall of the fornice 3 to allow the shell 6 to extend more posteriorly. This may require the use of an inserter (not shown) to give direction and placement into the posterior orbit and near the back of the eye 1.

Referring to FIG. 4, the device 6 is a dual or plural layer system enclosing one or more cavities 17 within which circulates the fluids for heat exchange. Within these cavities, there will be ridges 18 and channels 16 that redirect the circulating fluids to maximize heat-exchange. Thermal-regulation of the posterior portion of the eye 1 will be optimized via these channels 16, which may contain one-way valves and gates to redirect fluids. These features will allow for rapid as well as even or uneven distribution of fluids. The medium circulating within the thermal regulating device usually would be a liquid though gas could be dissolved or infused into solution to later propel such gas into surrounding tissue. Oxygen can be delivered through the conjunctiva and sclera effectively in this manner.

In another preferred embodiment, these channels 16, gates, or shell layers may have micropores/millipores 13 of various dimensions to allow selective filtration or passage of molecules of certain sizes.

In another embodiment, the outer coated layer 19 of the silicone rubber shell 6 can be coated with ceramic, lead, or another insulating material to maximize thermal regulation of the eye 1. For other purposes, the inner coated layer 20 or part thereof may be coated with ceramic, lead, or other insulating material to protect the eye or other structures from temperature changes when treating tissue outside of the eye 1.

In another preferred embodiment, the shell 6 can have an expandable posterior extension 35 that expands and pushes the fornices 3 posteriorly. This expansion can be achieved by positive pressure from the fluid circulating throughout the cavity or more directly from additional fluid inlet ports. Although the device is non-invasive, it can push the flexible and yielding ocular fornices 3 beyond the normal anatomical end-points effectively cooling the posterior retina, macula, vitreous, optic nerve 5, orbit, adnexae and other surrounding tissues.

A shell with a plurality of chambers and layers envelopes the eyeball, extending as far as possible to the superior and inferior fornices. If an incision of the posterior fornix is done, there will be extension of treatment beyond the conjunctiva and fornices 3 and a greater surface area can be treated by the device 6. It may drape over the eyelids in its anterior extension. This design combining the ocular shell and the eyelid speculum-like thermoregulating devices especially with iontophoresis may deliver anesthetics effectively to the eye, eyelids, orbital and periorbital areas. Preservative-free anesthetic agents can be delivered to the eye non-invasively and effectively to improve on current topical ocular anesthetic techniques.

The dual or plural layered system can provide both positive and negative pressure on the eye 1 by either pulsing or keeping a constant pressure. Eye-pressure measuring devices 11 can be incorporated into the encapsulating shell device 6 to monitor the intraocular pressure and regulate the fluids flowing through the device 6 to prevent excessive pressure on the eye 1.

Other embodiments of the shell design 6 include an integrated cooling system for the eye 1 and eyelid FIG. 16. The eyelid 2 may be cooled mainly by lid speculum 34 by holding the eyelid 2 apart. The thermally controlled fluid in this extension can be integrated with the rest of the shell's temperature-controlled system. It may drape over the eyelids in its anterior extension. This design combining the ocular shell and the eyelid speculum-like thermoregulating devices especially with iontophoresis may deliver anesthetics effectively to the eye, eyelids, orbital and periorbital areas. Preservative-free anesthetic agents can be delivered to the eye non-invasively and effectively to improve on current topical ocular anesthetic techniques Alternatively, in another preferred embodiment, the eyelid temperature-controlled system and the eye globe temperature-controlled system can be regulated separately by separate fluid pump systems to maximize the inner 20 and outer 19 shell's thermal-regulating effects to create differential cooling in different volumes of the eye and periorbital tissues.

In addition, separate temperature controls of two or more compartments within the shell 6 can create a temperature gradient if it is so desired. The temperature gradients can then influence the flow characteristics of fluids within the eye 1.

In another preferred embodiment of the device 6, the outer layer lid-speculum system 37 may be a separate unit with its own temperature-regulating system for the eyelids and nearby structures and doubly serves as an eyelid speculum 34. This system works in conjunction with a shell device 6 for the eye 1 to temperature regulate the eye 1 and the lid separately. This or another embodiment may use a clamp 40 for easy insertion and retraction of the device. This system in conjunction with a central opening 7 for the shell 6 allows the eye 1 to be exposed for therapeutic observation or intervention and treatment.

In another preferred embodiment, if the eye 1 is covered by a shell without a central opening and does not need to be exposed, the eye will have more efficient temperature control due to a greater surface area being treated. An outer thermal-regulating heat exchange pad 41 with channels 16 can cover the closed eyelid 2. A separate system for entry 42 and exit 43 ports are needed for this pad 41. However, an alternative integrated system 45 will incorporate both the pad 41 and shell 6. To secure this pad 41 a zip-lock system 44 may be used.

This outer device 41 may be loosely or firmly placed on or near the eyelid 2 as a pad or patch with the help of adhesives, suction mechanisms or other mechanical means. Within the cavities 17 there will be ridges 18 and channels 16 that redirect the circulating fluids to maximize heat-exchange.

Alternatively, in another preferred embodiment, a conductive heat-exchange system 46 can encapsulate the eyelid 2 forming a complete sealed system with the use of a vacuum chamber 47 whereby fluid 48 can freely circulate directly around the eye 1 for the purpose of cooling, heating, drug-delivery, irrigating, and other functions. The sealing can be accomplished with a zip-lock system 44, a suction-aided system 46, a mechanical clamp 40 or other mechanical means to form a cavity bordered by said device anteriorly and the eye posteriorly. The suction system 46 is accomplished by removing air via the vacuum port 49 by creating a vacuum in the vacuum chamber 47.

An anesthetic solution and/or gel can be applied to the eye 1 to prepare for the insertion of the device 6. The anesthetic material may be coated on the shell 6 prior to insertion beneath the lids 2. Commercially available anesthetic solutions such as Proparacaine or Tetracaine and anesthetic gels such as Lidocaine are readily available.

The eyelid 2, ocular surface and surrounding areas are then properly cleansed with antiseptic solutions such as Betadine and properly covered with a sterile drape. Other techniques are available and can be chosen according to the desired level of topical and local anesthesia.

For example, peri-bulbar or retro-bulbar injection of Lidocaine and Bupivacaine can achieve very deep and complete local anesthetic effects. Alternatively, a Tenon's infiltration of local anesthetics with a blunt Greenbaum cannula has essentially no risk of globe perforation yet quite effectively renders deep local anesthesia. In addition, an anesthetic lid block may be desirable in certain situations to facilitate eyelid speculum 34 and device 6 insertions and maintenance.

With the eyelid 2 manually separated, the device 6 is inserted into the cavity surrounding the globe. The shape of the device 6 takes advantage of the different posterior depths of the fornices 3 in different quadrants to maximize its reach. Depending upon its use, the device 6 can be prefabricated to have a less protracting depth. The device 6 can reach deeper in this sequence: medially, inferiorly, superiorly and laterally.

Medially, the medial canthal tendons tend to limit the posterior reach while temporally and superiorly, the extensions of the fornices are quite posterior. In one technique, the eyelids 2 are allowed to stay closed throughout the procedure. Alternatively, a standard lid speculum or a thermal-regulating device shaped similarly to a speculum 34 is inserted to keep the eyelid 2 apart followed by insertion of the thermal-regulating shell 6.

Further, the combined thermal regulating-eyelid speculum devices 34 as shown in FIG. 14 through 19 may be used to keep the eyelid 2 apart. FIGS. 16 and 17 show the same device as FIG. 14 with the addition of a ring base 36 or other suitable rigid or semi-rigid geometry that can support various diagnostic or surgical devices including but not limited to a gonioscope, viewing prisms, fundus contact lenses, medication wells, and others.

In the embodiment shown in FIG. 18, a shell with a plurality of chambers and layers envelopes the eyeball, extending as far as possible to the superior and inferior fornices and drapes over the eyelids in its anterior extension. This design combining the ocular shell and the eyelid speculum-like thermoregulating devices with iontophoresis may deliver anesthetics effectively to the eye, eyelids, orbital and periorbital areas. Preservative-free anesthetic agents can be delivered to the eye non-invasively and effectively to improve on current topical ocular anesthetic techniques. Combined with hypothermia, the method is much more effective than preoperative topical application of semi-frozen balanced salt solution (BSS) by some refractive surgeons to reduce pain after epi-LASIK or other refractive procedure.

This preferred embodiment may work very well for daily routine use in ophthalmic surgery. For example, prolonged vitreo-retinal surgeries in eyes already compromised by ischemic ocular conditions may benefit from hypothermal management of the posterior retina, macula, and optic nerve. Ganglion cells and retinal nerve fiber layers may be prone to injury from post-operative pressure rise.

For many years, the sclera and conjunctivae, in contrast to the corneal barrier, are known to be quite permeable to even large biological molecules. There are many advantages of combining hypothermia with iontophoresis. Previous iontophoretis attempts without hypothermia have invariably resulted in ocular burn. One object of this patent is to teach the advantages of combining these two technologies.

An effective transscleral drug delivery is desirable to avoid more invasive delivery routes. The delivery systems in accordance with the present invention combine the beneficial effects of tissue thermal regulation and iontophoresis-assisted penetration of medications and other biochemical agents. A thermal regulating device conforming to the eyeball and eyelids, can contain permeable cells filled with a medicament and can be equipped with an iontophoresis bioelectrode connected to a dose controller device which is battery-operated or which can be powered via an electric outlet. Medications, which are charged or can be charged and delivered iontophoretically, include but are not limited to steroids, non-steroidal anti-inflammatory agents, anti-vascular endothelial growth factors (anti-VEGF), other growth factors, hormones, anti-viral agents, antibiotics, anti-fungal agents, transvective therapeutics, anesthetics and other pharmaceutical agents. As another example, anterior segment eye surgeons are now performing many of their procedures with topical or intra-cameral anesthetics. To enhance this anesthetic effect, the eyeball shell/eyelid device can be used to concurrently iontophorese the eyelid and the eyeball with anesthetics and as well as suppress the sensory nerve endings of the eye and eyelids.

Although there has been hereinabove described a specific medical device and method for temperature control, medicament delivery and treatment of the eye and surrounding tissues in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A method for administrating a medicament to an eye comprising;
    inserting a shell over the sclera and retina of the eye;
    cooling of the eye and orbit by circulating fluid within the shell; and
    concurrently administering a medicament to the eye through the sclera and retina via magnetic drug delivery.

2. A medical device for administrating a medicament to an eye, the device comprising:
    a shell sized and shaped to conform to the sclera and retina of an eye, said shell having a posterior opening for enabling positioning of said shell over said eye;
    a source of cooling fluid;
    a fluid entry port and a fluid exit port, both in fluid communication with said shell, for circulating the cooling fluid through said shell in order to cool the eye; and
    magnetic apparatus for concurrently administering a medicament to the eye.

3. The medical device according to claim 2 wherein the apparatus for administering a medicament comprises a source of medicament disposed within said shell, and a magnet disposed in said shell and oriented in order that magnetic field of the magnet directs and controls ionic flow.

4. The medical device according to claim 3 wherein a plurality of magnets are provided, each magnet comprises a flat plate with polarity parallel to a thickness of each plate.

5. The medical device according to claim 3 wherein a plurality of magnets are provided, each magnet comprises a annular ring.

6. The medical device according to claim 3 wherein the magnet comprises a molded shell.

7. The medical device according to claim 3 wherein the means for administering a medicament further comprises a medicament barrier disposed in said shell exterior to the magnet.

8. A medical device for administering a medicament to an eye, the device comprising:
- a shell sized and shaped to conform to the sclera and retina of an eye, said shell having a posterior opening for enabling positioning of said shell over the eye;
- a thermoelectric cooler disposed in said shell for cooling the eye; and
- magnetic apparatus for concurrently administering a medicament to the eye.

9. The medical device according to claim 8 wherein the apparatus for administering a medicament comprises a source of medicament disposed within said shell, and a magnet disposed in said shell and oriented in order that magnetic field of the magnet directs and controls ionic flow.

10. The medical device according to claim 9 wherein a plurality of magnets are provided, each magnet comprises a flat plate with polarity parallel to a thickness of each plate.

11. The medical device according to claim 9 wherein a plurality of magnets are provided, each magnet comprises a annular ring.

12. The medical device according to claim 9 wherein the magnet comprises a molded shell.

13. The medical device according to claim 9 wherein the means for administering a medicament further comprises a medicament barrier disposed in said shell exterior to the magnet.

14. The medical device according to claim 3 wherein said magnet comprises electromagnetic coils.

15. The medical device according to claim 9 wherein said magnet comprises electromagnetic coils.

* * * * *